US012603172B2

(12) United States Patent
    Sonnenschein et al.

(10) Patent No.:     US 12,603,172 B2
(45) Date of Patent:         Apr. 14, 2026

(54) SYSTEM AND A METHOD FOR ALLOWING A NON-SKILLED USER TO ACQUIRE ULTRASOUND IMAGES OF INTERNAL ORGANS OF A HUMAN BODY

(71) Applicant: PULSENMORE LTD, Omer (IL)

(72) Inventors: Elazar Sonnenschein, Omer (IL);
                Yehuda Albeck, Kfar Adumim (IL);
                Paz Elia, Mazkeret Batya (IL);
                Menachem Becher, Carmit (IL)

(73) Assignee: PULSENMORE LTD, Omer (IL)

( * ) Notice:   Subject to any disclaimer, the term of this patent is extended or adjusted under 35 U.S.C. 154(b) by 0 days.

(21) Appl. No.:    17/920,951

(22) PCT Filed:    Apr. 25, 2021

(86) PCT No.:      PCT/IL2021/050470
     § 371 (c)(1),
     (2) Date:     Oct. 24, 2022

(87) PCT Pub. No.: WO2021/220264
     PCT Pub. Date: Nov. 4, 2021

(65)              Prior Publication Data
     US 2023/0165565 A1      Jun. 1, 2023

(30)        Foreign Application Priority Data
     May 1, 2020    (IL) ......................................... 274382

(51) Int. Cl.
     *G16H 40/67*          (2018.01)
     *A61B 8/00*           (2006.01)
                           (Continued)
(52) U.S. Cl.
     CPC ............... *G16H 40/67* (2018.01); *A61B 8/42* (2013.01); *A61B 8/4254* (2013.01);
                           (Continued)

(58) Field of Classification Search
     CPC ........ G16H 40/67; A61B 8/42; A61B 8/4254;
                 A61B 8/4263; A61B 8/4281; A61B
                                                8/429;
                           (Continued)

(56)              References Cited

U.S. PATENT DOCUMENTS 6,122,538  A     9/2000  Sliwa, Jr. et al.
     6,126,608  A    10/2000  Kemme et al.
                           (Continued)

FOREIGN PATENT DOCUMENTS

CA        2866370 A1     9/2013
     CN      104883982 A      9/2015
                           (Continued)

OTHER PUBLICATIONS

PCT International Search Report and Written Opinion for corresponding PCT Application No. PCT/IL2021/050469, mailed on Jul. 28, 2021, 12 pages.
                           (Continued)

*Primary Examiner* — Dixomara Vargas
(74) *Attorney, Agent, or Firm* — Dority & Manning, P.A.

(57)              ABSTRACT

A system for allowing a non-skilled user to acquire ultrasound images of internal organs of a human body comprises a scanner, at least one inertial measurement unit (IMU) associated therewith, a processor containing software, and a user interface comprising a display screen and means to accept user's instructions, wherein the software is configured to execute at least one of the following: to produce ultrasound images; to analyze the data; to decide which images are of sufficient quality to be displayed on the display screen; to discard low quality images; to instruct the operator to hold the housing of the scanner in a predetermined manner; to compute the location and attitude of the scanner; to determine if the scanner is being held such that enough
                           (Continued)

pressure is being exerted on the skin to produce an image of sufficient quality; and to effectively provide instructions how to move the scanner correctly in order to obtain satisfactory images.

15 Claims, 10 Drawing Sheets

(51) Int. Cl.

| | | |
|---|---|---|
| *G06T 11/00* | (2006.01) | |
| *G16H 30/20* | (2018.01) | |
| *G06V 10/40* | (2022.01) | |

(52) U.S. Cl.
CPC .......... *A61B 8/4263* (2013.01); *A61B 8/4281* (2013.01); *A61B 8/429* (2013.01); *A61B 8/4427* (2013.01); *A61B 8/4455* (2013.01); *A61B 8/461* (2013.01); *A61B 8/465* (2013.01); *A61B 8/5276* (2013.01); *A61B 8/56* (2013.01); *A61B 8/565* (2013.01); *A61B 8/58* (2013.01); *A61B 8/585* (2013.01); *G06T 11/00* (2013.01); *G16H 30/20* (2018.01); *A61B 2562/0219* (2013.01); *A61B 2562/0247* (2013.01); *G06T 2210/41* (2013.01); *G06V 10/40* (2022.01)

(58) Field of Classification Search
CPC ......... A61B 8/465; A61B 8/5276; A61B 8/56; A61B 8/585
See application file for complete search history.

(56) References Cited

U.S. PATENT DOCUMENTS

| | | | | |
|---|---|---|---|---|
| 9,877,700 | B1 | 1/2018 | Asch et al. | |
| 2002/0049382 | A1* | 4/2002 | Suh | A61B 5/4514 |
| | | | | 600/449 |
| 2008/0281206 | A1 | 11/2008 | Bartlett et al. | |
| 2009/0306509 | A1 | 12/2009 | Pedersen et al. | |
| 2012/0083692 | A1 | 4/2012 | Stoll | |
| 2012/0179039 | A1 | 7/2012 | Pelissier et al. | |
| 2013/0065211 | A1* | 3/2013 | Amso | G09B 23/286 |
| | | | | 434/262 |
| 2013/0158363 | A1 | 6/2013 | Zoghbi | |
| 2013/0237811 | A1 | 9/2013 | Mihailescu et al. | |
| 2014/0037168 | A1 | 2/2014 | Ishikawa et al. | |
| 2014/0058264 | A1 | 2/2014 | Baym et al. | |
| 2014/0087342 | A1* | 3/2014 | Campanatti, Jr. | G09B 23/00 |
| | | | | 434/262 |
| 2014/0114193 | A1 | 4/2014 | Anthony et al. | |
| 2014/0282018 | A1 | 9/2014 | Amble et al. | |
| 2015/0216512 | A1 | 8/2015 | Luo et al. | |
| 2015/0223772 | A1 | 8/2015 | Shi | |
| 2016/0213349 | A1 | 7/2016 | Groberman et al. | |
| 2016/0278739 | A1 | 9/2016 | Pelissier et al. | |
| 2016/0314715 | A1 | 10/2016 | Savitsky et al. | |
| 2017/0105701 | A1 | 4/2017 | Pelissier et al. | |
| 2017/0131094 | A1 | 5/2017 | Kulik | |
| 2017/0187530 | A1 | 6/2017 | Ghosh et al. | |
| 2017/0273663 | A1 | 9/2017 | Baym et al. | |
| 2017/0273664 | A1 | 9/2017 | Baym et al. | |
| 2017/0360401 | A1 | 12/2017 | Rothberg et al. | |
| 2017/0360402 | A1 | 12/2017 | De Jonge et al. | |
| 2018/0014811 | A1 | 1/2018 | Sonnenschein | |
| 2018/0132724 | A1 | 5/2018 | Waechter-Stehle et al. | |
| 2018/0153504 | A1 | 6/2018 | Cherry | |
| 2018/0168546 | A1 | 6/2018 | Ebata | |
| 2018/0344286 | A1 | 12/2018 | Mienkina et al. | |
| 2019/0059851 | A1 | 2/2019 | Rothberg | |
| 2019/0069842 | A1 | 3/2019 | Rothberg et al. | |
| 2019/0175144 | A1* | 6/2019 | O'Brien | A61B 8/0816 |
| 2019/0190952 | A1 | 6/2019 | Cherry | |
| 2019/0196600 | A1* | 6/2019 | Rothberg | G06V 40/20 |
| 2019/0328361 | A1 | 10/2019 | Halmann et al. | |
| 2020/0037987 | A1 | 2/2020 | Silberman et al. | |
| 2020/0069291 | A1* | 3/2020 | Zaslavsky | A61B 8/4245 |
| 2021/0041558 | A1* | 2/2021 | Akkaraju | A61B 8/08 |
| 2021/0145608 | A1* | 5/2021 | Herr | A61B 8/0825 |

FOREIGN PATENT DOCUMENTS

| | | | |
|---|---|---|---|
| CN | 109073410 | A | 12/2018 |
| CN | 109646047 | A | 4/2019 |
| CN | 109674494 | A | 4/2019 |
| CN | 109813336 | A | 5/2019 |
| CN | 109963514 | A | 7/2019 |
| CN | 110167449 | A | 8/2019 |
| CN | 110381846 | A | 10/2019 |
| CN | 110392552 | A | 10/2019 |
| CN | 110403630 | A | 11/2019 |
| CN | 110432928 | A | 11/2019 |
| CN | 110786887 | A | 2/2020 |
| CN | 111053573 | A | 4/2020 |
| CN | 115697206 | A | 2/2023 |
| EP | 3445249 | B1 | 4/2020 |
| JP | 2001276061 | A | 10/2001 |
| JP | 2010233609 | A | 10/2010 |
| JP | 2013240374 | A | 12/2013 |
| JP | 2014025791 | A | 2/2014 |
| JP | 2014150936 | A | 8/2014 |
| JP | 2015217306 | A | 12/2015 |
| JP | 2016503706 | A | 2/2016 |
| JP | 2017150484 | A | 8/2017 |
| JP | 2018020109 | A | 2/2018 |
| JP | 2018504185 | A | 2/2018 |
| JP | 2018509269 | A | 4/2018 |
| JP | 2018519664 | A | 7/2018 |
| JP | 2018519964 | A | 7/2018 |
| JP | 2018134386 | A | 8/2018 |
| JP | 2018520746 | A | 8/2018 |
| JP | 2019514476 | A | 6/2019 |
| JP | 2019514533 | A | 6/2019 |
| JP | 2019521745 | A | 8/2019 |
| WO | WO2006040967 | A1 | 4/2006 |
| WO | WO2014150961 | A1 | 9/2014 |
| WO | WO2015/142306 | | 9/2015 |
| WO | WO2017/163249 | | 9/2017 |
| WO | WO 2017/222970 | | 12/2017 |
| WO | WO2018089949 | A1 | 5/2018 |
| WO | WO2018091337 | A1 | 5/2018 |
| WO | WO2019/121127 | | 6/2019 |
| WO | WO2019/173152 | | 9/2019 |
| WO | WO 2019/223796 | A1 | 11/2019 |
| WO | WO 2020/023399 | A1 | 1/2020 |
| WO | WO2020016069 | A1 | 1/2020 |
| WO | WO2020/162989 | | 8/2020 |

OTHER PUBLICATIONS

Treece Graham M., et al., "Correction of Probe Pressure Artifacts in Freehand 3D Ultrasound," Medical Image Analysis 6.5 (2002), 199-214, Sep. 16, 2002—pp. 283-290.

Chinese Office Action (w/Machine Translation) for corresponding Application No. 202180032117.6, issued Jun. 27, 2025, 24 pages.

Ning Xialoin et al., "Advanced Filtering Methods and Their Applications in Navigation", with English translation, Apr. 30, 2019, national Defense Industry Press Publishing House, 16 pages.

Office Action received in corresponding Application No. CN 202180032117.6, dated Oct. 29, 2025, 20 pages.

* cited by examiner

SYSTEM AND A METHOD FOR ALLOWING A NON-SKILLED USER TO ACQUIRE ULTRASOUND IMAGES OF INTERNAL ORGANS OF A HUMAN BODY

CROSS REFERENCE TO RELATED APPLICATIONS

This application is a national stage of PCT Patent Application No. PCT/IL2021/050470, filed on Apr. 25, 2021, which, in turn, claims the right of priority to Israeli Patent Application No. 274382, filed on May 1, 2020, the entire contents of both of which are hereby incorporated herein by reference in their entirety for all purposes.

FIELD OF THE INVENTION

The invention is from the field of medical devices. Specifically, the invention relates to a system and method for accurately positioning and moving a hand-held ultrasound probe utilizing an inertial measurement unit.

BACKGROUND OF THE INVENTION

Knowing the location of a medical sensor or a medical device relative to a patient's anatomical structure and the speed with which the sensor or device is or should be moving is critical for the functionality of advanced remote control, robotic, autonomous, self-feedback, or other automatic medical procedures.

The speed at which an ultrasound probe (also referred to herein variously as "scanner," "ultrasound head," or simply "probe" for simplicity) moves across the body provides important information. For example, images taken at speed lower or higher than some range may be deleted or possibly be subject to special filtering and image processing techniques in order to enhance blurred images. Also, instruction may be provided to the operator concerning several aspects of the procedure such as when to stop movements, how to correct the scan path, how to change orientation or to tilt the probe, etc. In the case of remote control of an ultrasound probe or a sensor mounted on a gimbal located on a patient's body, knowing the two-dimensional or three-dimensional speed at which the ultrasound probe moves is also important to track the overall location, attitude and speed of the gimbal and/or the probe.

An extremely common procedure is ultrasound scanning, which inter alia nearly every woman undergoes during prenatal visits to her doctor or a clinic. Typically, in this scenario, an ultrasound technician (sonographer) or physician performs the scans. The operator, i.e. technician, midwife, doctor, sonographer, etc. knows, based on their experience, the best position and orientation in which the scanner head or probe must be located in order to image specific structures of the embryo, the right amount of pressure against the belly that is necessary to keep good coupling of the scanner to the body, the angle of the probe relatively to the belly, and the right scanning speed that will allow good imaging. Moreover, the operator sees the images generated by the probe on a screen in real time and is able to optimize or correct its position. Herein the term "probe" or "ultrasound probe" refers to any useful probe, linear or convex, phase array, HIFU, or other sensor.

In the context of this description the term "scanner," should be understood to refer to an element, housing or device, which must move over the surface of a patient's body to acquire data therefrom, e.g., ultrasound images.

Many scans take place just to monitor the embryo's vitality signs, e.g. heartbeat, movement, amniotic fluid volume, tone, and respiration. These scans could also be executed by the patient at her home or other location that is not a clinic, hospital or medical facility, thus saving the overloaded medical system time and resources, and potentially avoiding an unnecessary visit to an emergency department or a prenatal visit to the doctor's office, a clinic or a hospital. However, performing an ultrasound scan requires some of the ultrasound operator's skill that untrained persons lack. It is clear that it would be highly desirable to provide means by which an unskilled person can perform a "do-it-yourself" ultrasound scan that yields useful results.

It is therefore a purpose of the present invention to provide a device and method that assist a patient in performing an ultrasound scan by monitoring the motion of the scanner head (ultrasound probe) and providing feedback that assists in positioning the scanner head at the desired location.

Further purposes and advantages of this invention will appear as the description proceeds.

SUMMARY OF THE INVENTION

In a first aspect the invention encompasses a system for allowing a non-skilled user to acquire ultrasound images of internal organs of a human body, comprising a scanner, at least one inertial measurement unit (IMU) associated therewith, a processor containing software, and a user interface comprising a display screen and means to accept user's instructions, wherein the software is configured to execute at least one of the following: to produce ultrasound images; to analyze the data; to decide which images are of sufficient quality to be displayed on the display screen; to discard low quality images; to instruct the operator to hold the housing of the scanner in a predetermined manner; to compute the location and attitude of the scanner; to determine if the scanner is being held such that enough pressure is being exerted on the skin to produce an image of sufficient quality; and to effectively provide instructions how to move the scanner correctly in order to obtain satisfactory images.

In one embodiment, the system comprises an electronic communication component selected from one or more of USB, Lightning, fiber optic, Wi-Fi, UWB, Bluetooth and IR.

In a first aspect the invention encompasses a system for acquiring ultrasound images of internal organs of a human body. The system comprises a scanner and at least one inertial measurement unit (IMU) associated therewith.

In some embodiments of the system the at least one IMU is one of: a) integral with the scanner; b) connected to the scanner via a plug-in connection; and c) provided in an element associated with the scanner and moving therewith during operation.

Some embodiments of the system are configured to issue instructions to the operator of the system that allow scans to be performed also by persons not trained for ultrasound scanning including the patient themselves.

In some embodiments of the system wherein the scans are performed by untrained operators, the scans are transmitted to a remote location for analysis by a healthcare professional.

Some embodiments of the system are configured to allow two-way communication between the operator and a remote individual or non-monitored system, wherein the non-monitored system comprises automated, image analysis circuitry. The two-way communication can be selected from audio, visual, and video communication, and combinations thereof.

In some embodiments of the system, when the scans are performed by untrained operators, two way video communication is enabled between the operator and the health care professional, enabling them to see each other while the operator is carrying out the scanning procedure to aid the health care professional in interpreting the images and to provide guidance if necessary. In some embodiments the system is configured such that the output of the system is sent directly to a remote healthcare professional and/or to a non-monitored system either in real time or after the images are acquired.

Some embodiments of the system are configured to overlay an image of the scanner on top of the ultrasound scans to aid a healthcare professional in interpreting the images.

Embodiments of the scanner of the system comprise a housing that is ergonomically designed to be held by an operator and moved across the skin of a person or animal. Some embodiments of the housing comprise, or has associated therewith, at least the minimum number of components of the system that must be located on the patient's body to obtain the ultrasound images. In some embodiments of the housing the minimum number of components in, or associated with the housing are: i) an ultrasound probe head; ii) the at least one IMU, which comprises a three-axis accelerometer and a three-axis gyroscope; iii) electronic components for wired or wireless communication with remote terminals, and iv) a power source.

When referring to an "ultrasound probe head," the term should be understood in its broadest meaning to include, for instance, a single element, 1D, 1.5D, 2D, 3D, and a phased array probe, as well as any other arrangement that may be used for the purposes of the invention.

In some embodiments of the system the housing comprises other components that may be arranged in many different configurations in which at least some of them may be located within the housing. In these embodiments the other components of the system are: v) an Analog Front End (AFE) that transmits and receives ultrasound signals by means of electronic components; vi) a processor containing software; vii) a user interface comprising a display screen and means to accept user's instructions; and viii) at least one memory device to store data and images processed by the software in the processor. In these embodiments the other components that are not located within the housing are located at a location near the patient but separated from the housing. In these embodiments the other components that are not located within the housing are in communication with components located within, or associated with the housing.

In some embodiments of the system the electronic components of the AFE comprise transmitters, receivers, amplifiers, and analog to digital (A/D and digital to analog (D/A) converters.

In some embodiments of the system the software is configured to operate the system and to receive and process ultrasound signals received from the AFE to produce ultrasound images and to receive and process inertial measurement signals received from the IMU.

In some embodiments of the system the AFE, IMU, processor, memory devices, and communication components can be provided as separate integrated circuits (ICs) or integrated into one or more ASICs that comprise at least some of the ICs.

Some embodiments of the system comprise additional components. The additional components comprise at least one of: ix) a remote terminal; x) at least one additional IMU; xi) at least one three-axis magnetometer; xii) at least one pressure sensor; and xiii) a speaker and a microphone for communicating with a remote health care provider.

In some embodiments of the system all of the other components v)—viii) are contained within a remote terminal, which is connected to the scanner via a wired or wireless communication link. In other embodiments of the system some of the other components v)—viii) are contained within the scanner and the remainder located at a remote terminal, which is connected to the scanner via a wired or wireless communication link.

In some embodiments of the system the remote terminal is a portable communication device. In some embodiments of the system the portable communication device is a smartphone. In some embodiments of the system the portable communication device comprises the display, the IMU, and the processor. In some embodiments of the system the portable communication device fits into a socket in the housing of the scanner. In some embodiments of the system the portable communication device is an integral part of the housing. In some embodiments of the system the portable communication device is not an integral part of the housing, but is fit into the socket in the housing before performing a scan, moved together with the housing during an ultrasound scan, and if desired, later detached for other uses. In some embodiments of the system the portable communication device is connected via a cable or wireless connection to the housing and only the housing is moved.

Illustrative examples of suitable wired communication links include USB, lightning, and fiber optic, but, of course, any additional wired communication is possible. Illustrative examples of wireless communication links include, but are not limited to, Wi-Fi, UWB, Bluetooth, and IR.

The portable communication device can be any of many suitable devices, for example, a mobile phone, tablet, laptop. Moreover, the housing or a device connected therewith, may be in communication with apparatus located in the cloud, adapted to receive data generated by, or in association with, the housing.

In some embodiments of the system different combinations of one or more IMUs, processing devices and software, memory devices, power sources, and components of the AFE are located either within the housing or in the smartphone. Some embodiments of the system comprise at least one IMU in the smartphone and at least one IMU in the housing.

In some embodiments of the system the processor is configured to receive data collected by all sensors.

In some embodiments of the system the software is configured to execute at least one of the following: to produce ultrasound images; to analyze the data; to decide which images are of sufficient quality to be displayed on the display screen; to discard low quality images; to instruct the operator to hold the housing of the scanner in a predetermined manner; to compute the location and attitude of the scanner; to determine if the scanner is being held such that enough pressure is being exerted on the skin to produce an image of sufficient quality; and to effectively provide instructions how to move the scanner correctly in order to obtain satisfactory results.

The term "of sufficient quality" refers to images that in whole, or from elements thereof, allow deducing, automatically or by a professional viewing them, an anatomical structure or a physiological condition.

Some illustrative and not exhaustive examples of matters that can be deduced from the image include fetal heart detection, fetal heart rate measurement, amniotic fluid measurement, fetal movement detection, measurement of blood flow direction and velocity in the fetal heart and arteries, detection of lumps in the thyroid gland, detection of abnormal cells in the skin, abnormal prostate structure, liquid in the lung, etc.

In some embodiments of the system instructions to the operator that are generated by the software are provided visually on the display screen or audibly from the speakers. In some embodiments of the system instructions to the operator are provided visually on the display screen or audibly from the speakers by a trained health care professional located at a remote terminal.

In some embodiments of the system the task of computing the navigation, including the scanner's location, orientation, and time derivatives of them, is carried out by an Inertial Navigation System (INS) comprising a set of three-axis gyroscopes and three-axis accelerometers in the IMU and other sensors; the processor; and software, which is configured to take initial conditions and calibration data and the output from the IMU and other sensors to compute the Navigation, wherein the other sensors can be at least one of a three-axis magnetometer, a pressure sensor, and a camera.

Some embodiments of the system are configured to generate accurate scans of ultrasound signals on the skin and to ensure good value images for diagnostic purposes by using a combination of a pressure sensor and IMU and selecting only images that meet optimal values of the speed of scanning and pressure of the scanner against the skin.

In some embodiments of the system the INS provides the following types of data:

a. angles of orientation;
b. speed of the scanner; and
c. location of the ultrasound probe head relative to the body's anatomy.

In some embodiments of the system the speed of the scan is calculated from the angular velocity assuming motion perpendicular to the surface of the body.

In some embodiments of the system, for prenatal exams, the body is modeled as a sphere, whose radius can be approximated by one or more of the patient's BMI, the stage of the pregnancy, or a visual estimate, e.g. in the range of 20 cm up to 70 cm for obese patients.

In some embodiments of the system typical distances for the scans are in the range of several millimeters up to several tens of centimeters. In some embodiments of the system the speed of the scan is between 1 mm per second and several centimeters per second.

In some embodiments of the system the 3-axis gyroscopes and 3-axis accelerometers of the IMU are calibrated by the manufacturer for offset, scale-factor, cross-axis sensitivity and initial orientation; and MEMS IMUs are calibrated by the user before each scan. In some embodiments of the system, if the motion of the scan is slow and the operator maintains the orientation of the scanner relative to the body being scanned within a several degrees of a predetermined starting orientation, then a one-step calibration, in which only the offset of the gyroscopes is estimated, is required, wherein the one-step calibration process comprises holding the IMU still for several minutes and recording the output of the sensors; wherein the average output of the gyroscopes is taken to be their offset and the variance of each sensor is taken to be its noise.

In some embodiments of the system the operator performs a seven-phase calibration process, wherein the seven phases of the calibration process in a coordinate system wherein the positive Z-axis points up, the positive Y-axis points towards the right, and the positive X-axis points forward are:

a. Phase 1: hold the scanner still for T seconds;
b. Phase 2: rotate the scanner around the Y axis such that the rotation is completed, and the scanner is stationary in the new orientation, within T seconds;
c. Phase 3: hold the scanner still for T seconds, then rotate back;
d. Phase 4: rotate the scanner over around X axis within T seconds;
e. Phase 5: hold the scanner still for T seconds, then rotate back;
f. Phase 6: rotate the scanner over around Z axis within T seconds; and
g. Phase 7: hold the scanner still for T seconds, then rotate back.

In some embodiments of the system, if the processor determines, during a scan, that not enough pressure is being exerted on the skin, an instruction to increase the pressure is issued to the operator either visually on the display screen, e.g. by displaying a downward pointing arrow, and/or audibly from the speakers. In these embodiments the processor can determine that not enough pressure is being exerted on the skin by at least one of:

a. analyzing the image and determining that the picture is flat; and
b. measuring the variance of the brightness of the image over some region of interest in the image and determining that the variance is smaller than a threshold value; or
c. by histogram threshold, i.e., by measuring each pixel value in a region of interest and determining a threshold requiring an alert.

The term "flat" as used herein means that, because of the insufficient pressure on the skin, the ultrasound wave does not reach the required depth and, as a result, the image obtained does not show the internal organ or fetus that the user is attempting to image.

In some embodiments of the system the processor contains software configured to determine if an insufficient quantity of water-based gel is interposed between the ultrasound probe head and the skin and to issue an alert to the operator either visually on the display screen and/or audibly from the speakers. In these embodiments the software can determine if an insufficient quantity of water-based gel is interposed between the ultrasound probe head and the skin by determining if there is weakening of the signals returning to the probe or weakening of the resulting ultrasound image.

In some embodiments the system comprises an IMU-independent component adapted to alert the user in case of insufficient coupling between the apparatus and the body. In other embodiments the system comprises an IMU-independent component adapted to alert the user if the scanning speed it too fast.

In some embodiments of the system the processor and software of the system are configured to issue the following set of instructions to guide an operator to perform a scan:

a. instruct the operator to carry out a calibration procedure if necessary by guiding the operator through the procedure;
b. instruct the operator to measure the patient's blood pressure, using a blood pressure meter;
c. instruct the operator to perform other analyses suggested by one or more details of an image;
d. instruct the operator how to position the patient to take the scan;
e. instruct the operator to position the scanner at a location that will serve as the center of a patient coordinate system;

f. instruct the patient to operator the scanner with the screen facing the patient;

g. provide the operator with instructions including the direction in which to move the scanner over the surface of the patient's body, how far to move in each direction, the speed with which the scanner should be moved, and the amount of force they should exert to press the scanner against the body;

h. advise the operator that the session is over when enough images of sufficient quality have been collected; and i. if not done so automatically, advise the operator to forward the images to a health care professional to be interpreted.

In a second aspect the invention encompasses a method for allowing a operator not trained for ultrasound scanning to obtain and process ultrasound images of internal organs of a human body. The method comprises:

a. providing a system comprised of a scanner and at least one inertial measurement unit (IMU); wherein, the scanner is the component of the system that is moved by an operator over the surface of a patient's body to obtain the ultrasound images, the at least one IMU is located within the scanner, and the system is configured to issue instructions to the operator of the system that allow scans to be performed;

b. follow the instructions issued by the system.

In an embodiment of the method of the second aspect, the system is the system of the first aspect of the invention.

In an embodiment of the method of the second aspect, the instructions issued by the system are the instructions issued by the processor and software of the system of the first aspect of the invention.

In a third aspect the invention encompasses a method for acquiring ultrasound images of internal organs of a human body. The method comprises providing a scanner and at least one inertial measurement unit (IMU) associated therewith, and instructions for an untrained user to operate said scanner.

Some embodiments of the third aspect of the method comprise issuing instructions to the operator of the system that allow scans to be performed also by persons not trained for ultrasound scanning including the patient themselves. Some embodiments of the method of the third aspect comprise transmitting acquired ultrasound images to a remote location for analysis by a healthcare professional. Some embodiments of the method of the third aspect comprise providing circuitry adapted to perform two-way communication between the user and a remote individual or non-monitored system. In some embodiments of the third aspect of the method the non-monitored system comprises automated, image analysis circuitry and the output of an automated analysis is provided to the user and/or to a healthcare professional. In some embodiments of the third aspect of the method the two-way communication is selected from audio, visual, and video communication, and combinations thereof.

In some embodiments of the third aspect of the method the scans are performed by untrained operators and the system enables two way video communications between the operator and a health care professional. In some embodiments of the third aspect of the method the output of the system is sent directly to a remote healthcare and/or to a non-monitored system professional in real time, or after the images are acquired.

In some embodiments of the third aspect of the method the system enables overlaying an image of the scanner on top of the ultrasound scans to aid a healthcare professional in interpreting the images.

In some embodiments the method comprises performing a calibration process on at least one axis in a coordinate system wherein the positive Z-axis points up, the positive Y-axis points towards the right, and the positive X-axis points forward, which are:

a. Phase 1: hold the scanner still for T seconds and then perform one or more of the following, for each axis:

b. Rotate the scanner around the selected axis such that the rotation is completed, and the scanner is stationary in the new orientation, within T seconds; and c. Hold the scanner still for T seconds, then rotate back;

In some embodiments of the third aspect of the method comprise performing a calibration process consisting of seven phases, in a coordinate system wherein the positive Z-axis points up, the positive Y-axis points towards the right, and the positive X-axis points forward, which are:

a. Phase 1: hold the scanner still for T seconds;

b. Phase 2: rotate the scanner around the Y axis such that. the rotation is completed, and the scanner is stationary in the new orientation, within T seconds;

c. Phase 3: hold the scanner still for T seconds, then rotate back;

d. Phase 4: rotate the scanner over around X axis within T seconds;

e. Phase 5: hold the scanner still for T seconds, then rotate back;

f. Phase 6: rotate the scanner over around Z axis within T seconds; and g. Phase 7: hold the scanner still for T seconds, then rotate back.

In some embodiments of the third aspect of the method, if the processor determines, during a scan, that not enough pressure is being exerted on the skin, an instruction to increase the pressure is issued to the operator either visually on the display screen, e.g. by displaying a downward pointing arrow, and/or audibly from the speakers. In these embodiments, determining whether the not enough pressure is being exerted on the skin can be by at least one of:

a. analyzing the image and determining that the picture is flat; and b. measuring the variance of the brightness of the image over some region of interest in the image and determining that the variance is smaller than a threshold value; or c. by histogram threshold, i.e., by measuring each pixel value in a region of interest and determining a threshold requiring an alert.

Some embodiments of the third aspect of the method comprise determining through software analysis if an insufficient quantity of water-based gel is interposed between the ultrasound probe head and the skin and issuing an alert to the operator either visually on the display screen and/or audibly from the speakers if an insufficiency of gel is found. In these embodiments of the third aspect of the method, the software can determine if an insufficient quantity of water-based gel is interposed between the ultrasound probe head and the skin by determining if there is weakening of the signals returning to the probe or weakening of the resulting ultrasound image.

Embodiments of the third aspect of the method comprise guiding an operator to perform a scan by issuing the following set of instructions:

a. instructing the operator to carry out a calibration procedure if necessary, by guiding the operator through the procedure;

b. instructing the operator to measure the patient's blood pressure, using a blood pressure meter;

c. instruct the operator to perform other analyses suggested by one or more details of an image;

d. instructing the operator how to position the patient to take the scan;

e. instructing the operator to position the scanner at a location that will serve as the center of a patient coordinate system;

f. instructing the operator to position the scanner with the screen facing the patient;

g. providing the operator with instructions including the direction in which to move the scanner over the surface of the patient's body, how far to move in each direction, the speed with which the scanner should be moved, and the amount of force they should exert to press the scanner against the body;

h. advising the operator that the session is over when enough images of sufficient quality have been collected; and i. if not done so automatically, advising the operator to forward the images to a health care professional to be interpreted.

All the above and other characteristics and advantages of the invention will be further understood through the following illustrative and non-limitative description of embodiments thereof, with reference to the appended drawings.

DETAILED DESCRIPTION OF EMBODIMENTS OF THE INVENTION

Herein the invention will be described in detail as a system and method that allow a patient to perform ultrasound scans by themselves. While a detailed example for ob-gyn is provided, a person skilled in the art can easily adapt it to other conditions and other organs, for example, cardiovascular, lungs, kidney, thyroid, liver, prostate, bladder, and for other sensors. Moreover, although conceived as a system for self—use by a person in a home environment, because of its portable nature, the system can also be effectively employed by persons not fully trained for ultrasound scanning, for example by a family member, in ambulances, or in the field by an untrained soldier. Needless to say that trained persons may also derive benefits from using the invention as a first approximation, before operating other, more sophisticated equipment available to them.

The other sensors referred to above can include any type of sensor that generates data that is useful in improving and/or add relevant information to that acquired through ultrasound images. For instance, blood pressure (the importance of which in the context of the invention will be further discussed below) can be transmitted to the device of the invention where it can be coupled or overlayed to other information, or can be used to alert the user and/or a health practitioner of any potential problems. Another example is a proximity sensor, which can be used to alert the user if not enough pressure is applied with the housing to the body, which may result in defective readings.

An additional example of a sensor useful in the context of the invention is an image acquisition element, which can be used, independently of IMU components, to alert the user of coupling problems (e.g., due to insufficient pressure of the device against the body or insufficient gel), or if the user is scanning too fast to generate a good quality image. The abovementioned and other situations that require alerting the user are detected via image processing, which can be performed locally in the housing or remotely by a connected device.

The scans can be performed by the patient themselves and then transmitted to a remote location for analysis by a health care professional or a non-monitored system, which comprises automated, image analysis circuitry. Some embodiments of the system are configured to allow the use of two-way video communication, i.e. Telemedicine, enabling the patient and a sonographer or to see each other while the patient is carrying out the scanning procedure.

Figure 9:
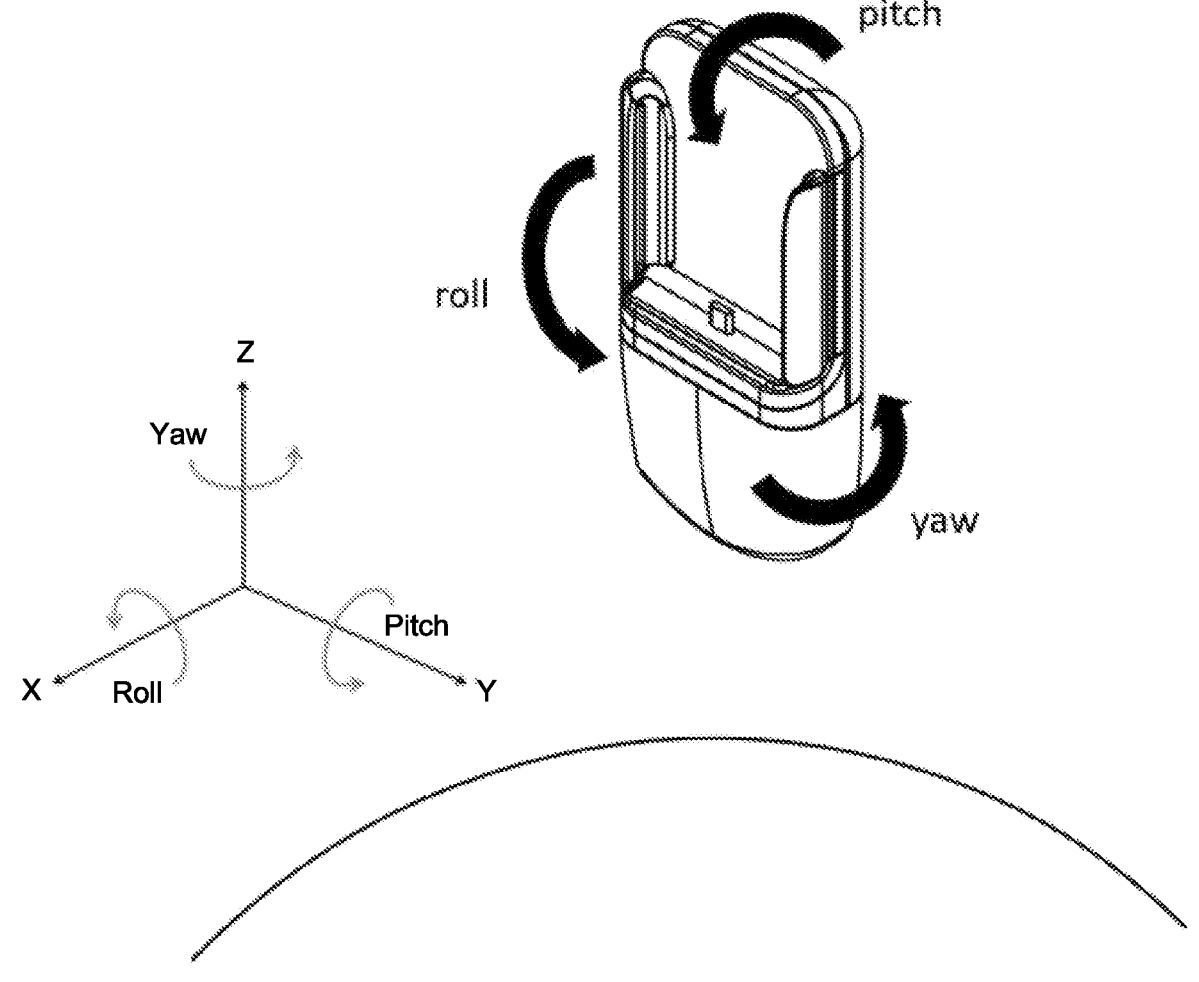
FIG. 9 illustrates movements of a scanner relative to patient's body.

The invention also encompasses a system for obtaining and processing ultrasound images of internal organs of a human body. The system is comprised of many components that are arranged in many different configurations, examples of which will be described herein. The component of the system that is essential to all configurations is called herein a "scanner," which comprises components of the system that are moved by an operator over the surface of a patient's body to acquire the ultrasound images. FIG. 9 illustrates the possible forms of movement of the scanner relative to the patient's body. The scanner comprises a housing that is ergonomically designed to be held by an operator and to be moved across the skin of a person or animal. The housing comprises at least the minimum number of components of the system that must be located on the patient's body to obtain the ultrasound images. These elements can be integral with the housing or associated therewith. In the context of this description, the term "associated with" should be interpreted as meaning that the elements or components to which it is referred must not necessarily be integral with the housing, but must be in useful cooperation therewith, For instance, where an accelerometer is discussed, it must move together with the housing, and when a communication component is discussed, it must be in communication with any other component located within the housing with which it must exchange data, or from which it must receive data. These components are: i) an ultrasound probe head, i.e. an array of ultrasound elements; ii) electronic components for wired or wireless communication with remote terminals, and iii) a power source, e.g. a battery when the system is wireless or power supply in case of wired system; and in most embodiments iv) at least one Inertial Measurement Unit (IMU) comprising the inertial sensors, i.e. a three-axis accelerometer and a three-axis gyroscope, and possibly other sensors, e.g. a three-axis magnetometer and a pressure sensor.

However, in some embodiments of the invention the inertial sensors are not integral with the housing. Instead, the inertial sensors of the smartphone or the like portable device (that will be discussed later) can be used, or add-on inertial sensors can be connected to the housing prior to use. In another embodiment of the invention, the housing can be a "docking housing," i.e., a housing that only comprises components essential for connecting functional components such as sensors of various types thereto, and said sensors can be connected to the docking housing as needed. This embodiment allows selecting appropriate kinds of sensors for a given use, which can be added as "plug and play" components to the housing.

Other typical components of the system are: v) an Analog Front End (AFE) that transmits and receives ultrasound signals by means of electronic components including, inter alia, transmitters (pulsers), receivers, amplifiers, and analog to digital (A/D and digital to analog (D/A) converters; vi) a processor containing software configured to operate the system and to receive and process ultrasound signals received from the AFE to produce ultrasound images and to receive and process inertial measurement signals received from the IMU; vii) a user interface comprising a display screen and means to accept user's instructions, e.g. a keyboard or touch screen; and viii) a memory device or devices to store data and images processed by the software in the processor. In different embodiments some or all of these components may be located within the housing of the scanner or at a location near the patient but separated from the housing. There are many options for arranging these components, which will be easily appreciated by the skilled person.

The electronic components, i.e. the AFE, IMU, processor, memory devices, and communication components can be provided as separate integrated circuits (ICs) or integrated into one more ASICs that comprise all or some of the ICs.

Optional components of the system include: ix) a remote terminal e.g. a smartphone, tablet, PC, or similar communication and computing device that is located near the operator or far from the operator, e.g. in a clinic or doctor's office; x) one or more additional IMUs; x) at least one three-axis magnetometer; xi) at least one pressure sensor; and xi) a speaker and microphone for communicating with a remote health care provider.

In some embodiments of the system all the components v)—viii) are contained within (or on in the case of the display) the housing of the scanner.

In some embodiments of the system all the components v)—viii) are contained within a remote terminal, which is connected to the scanner via a wired or wireless communication link; wherein the wireless link can be formed using any known technology, e.g. Cellular, WIFI or Bluetooth.

In some embodiments of the system some of the components v)—viii), e.g. some or all of the components of the AFE, are contained within the scanner and the remainder in the remote terminal, which is connected to the scanner via a wired or wireless communication link.

Figure 5:
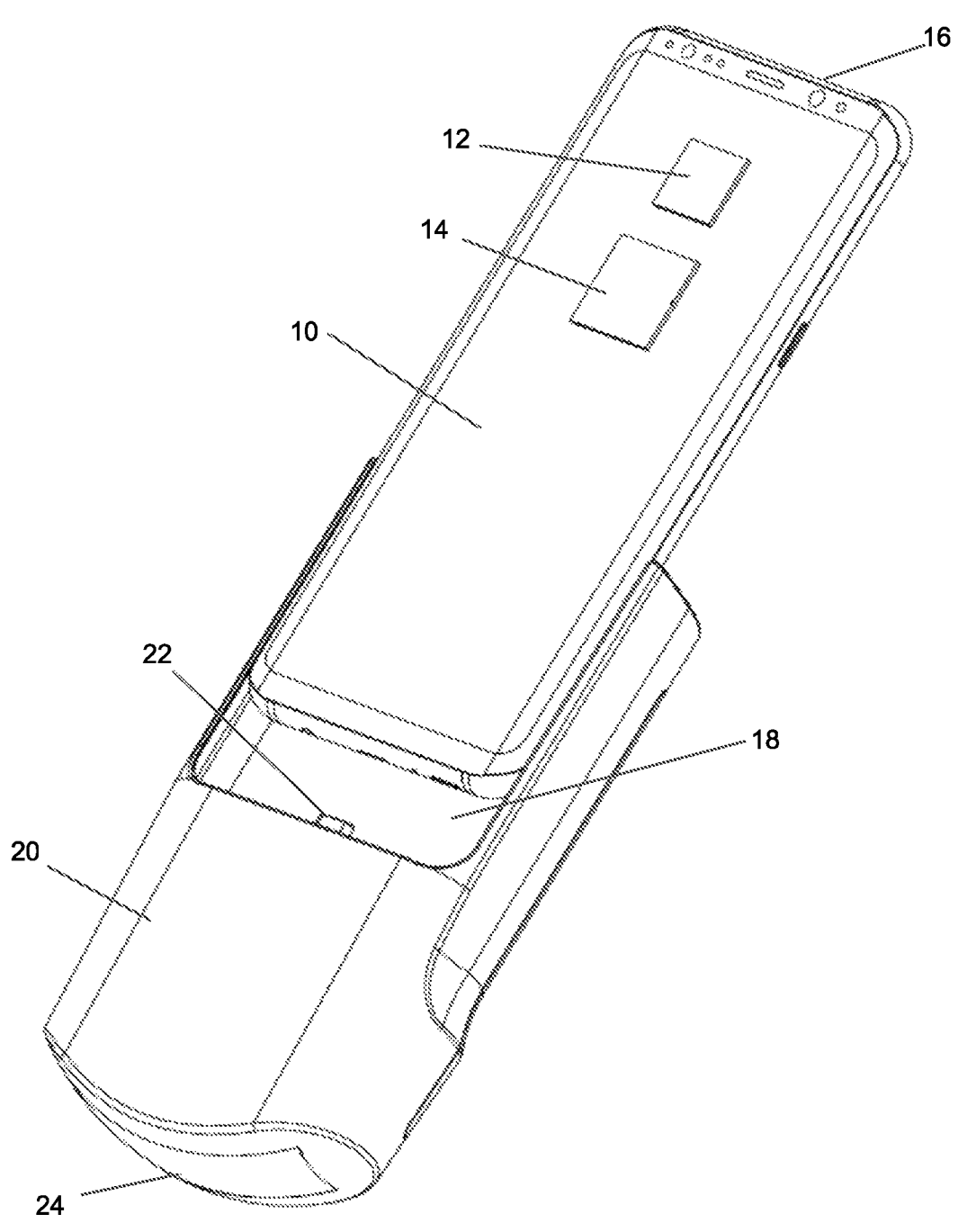
FIG. 5 schematically shows an embodiment in which a smartphone comprising components of the system fits into a socket in the housing of the scanner of the system.

FIG. 5 schematically shows an embodiment in which the display 10, an IMU 12, and the processor 14 are contained in a smartphone 16, which fits into a socket 18 in the housing 20 that contains the other components of the scanner. The smartphone 16 is not necessarily an integral part of the housing 20 but may be fit into the socket 18 before performing a scan, moved as an integral part of the housing 20 during an ultrasound scan, and later detached for other uses. The smartphone 16 is electrically connected to the housing 20 by a connector 22 in the socket 18, which fits into a standard port on the smartphone 16. Seen in FIG. 5 is ultrasound probe head 24 at the bottom of housing 20. The term "smartphone," as used herein, refers to any portable communication device for which a fitting seat can be created in a housing such as housing 20 of FIG. 5, and is not intended to limit the invention to any particular type of communication device, existing or to be developed. The smartphone was chosen in this example, to illustrate the invention only, since it is a widespread device available to most people.

In another embodiment the smartphone is connected via a cable or a wireless connection to the housing and only the housing or the probe itself is moved, i.e., the smartphone does not necessarily have to move in unison with the ultrasound probe.

In other embodiments, different combinations of one or more IMUs, processing devices and software, memory devices, power sources, and components of the AFE are located either within the housing or in the smartphone.

Because the IMU is, on the one hand, very noisy and, on the other hand, relatively inexpensive, in some embodiments it is advantageous to use several of them in one scanner, e.g. one IMU in the smartphone and another in the housing or two or more IMUs in the housing. This will increase the accuracy of the positioning and motion measurements and improve the signal-to-noise (S/N) ration of the received ultrasound signals.

The processor is configured to receive data collected by all sensors and contains software that is configured, inter alia, to produce ultrasound images; to analyze the data; and in some embodiments, to decide which images are of sufficient quality to be displayed on the display screen; to compute the location and attitude of the scanner, to discard low quality images; to instruct the operator to hold the housing of the scanner in a predetermined manner, e.g. such that the display screen (or a designated symbol on the housing surface in embodiments in which the display is remotely located) always faces her/him; to determine if the scanner is being held such that enough pressure is being exerted on the skin to produce an image of sufficient quality; and to effectively provide instructions how to move the scanner correctly in order to obtain satisfactory images by means of an intuitive graphical cue presented on the display screen. In other embodiments the instructions to the operator are provided visually or audibly on the display screen and speakers or by a trained health care professional located at a remote terminal.

Figure 6:
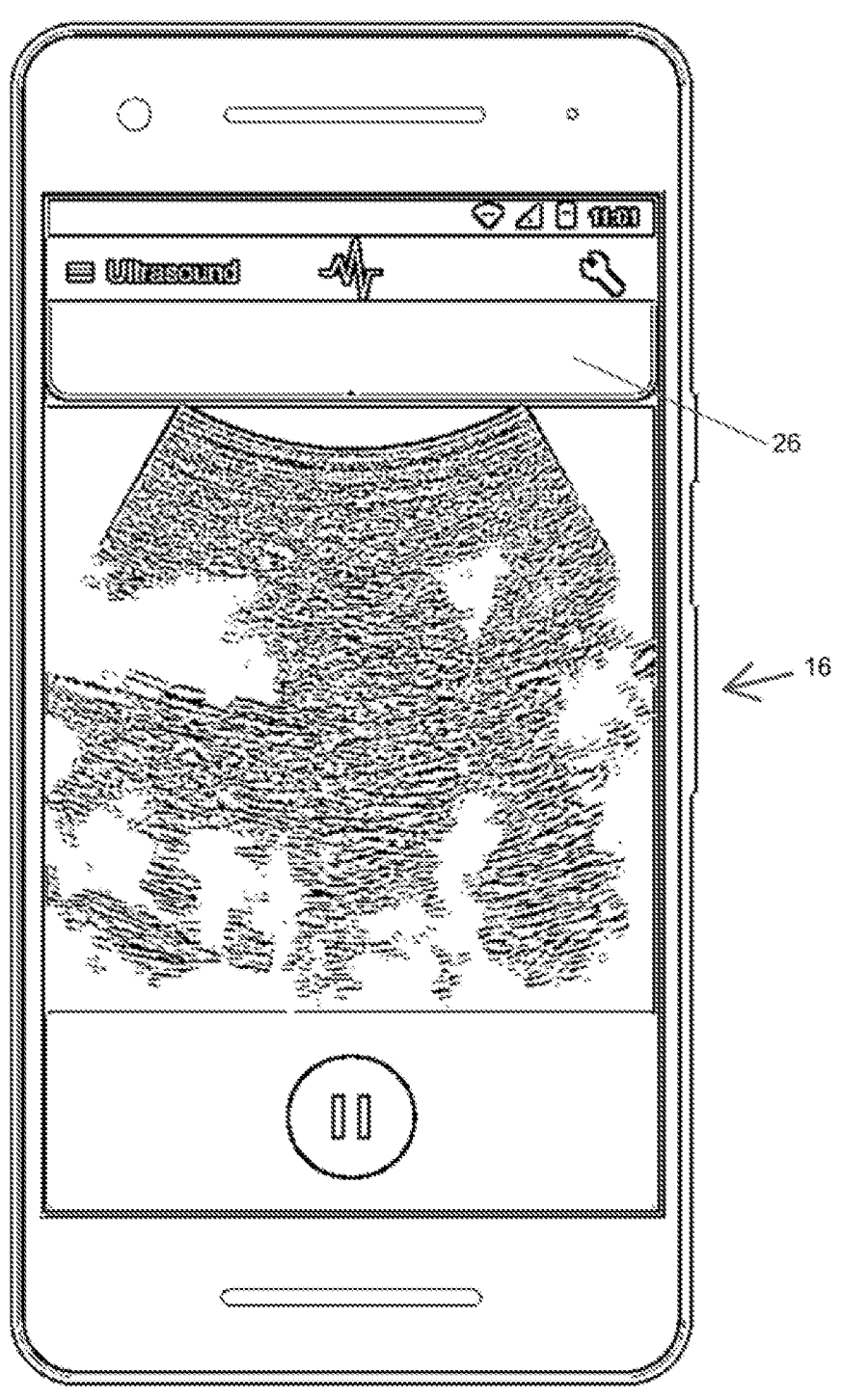
FIG. 6 schematically shows a typical scene on the screen of a smartphone during a scan with the embodiment of the system shown in FIG. 5.

FIG. 6 schematically shows a typical scene on the screen of a smartphone 16 during a scan with the embodiment of the system shown in FIG. 5. The blank area 26 on the screen is reserved, in this illustrative embodiment, for instructions to the user from the system. Typical instructions include, for example:

The screen is not facing you—please keep it perpendicular to your body;

The image is not clear—please apply more pressure or add more gel;

You're moving too fast—please slow down; and

Please move the housing to the right.

The task of computing the scanner's location, orientation, and time derivatives of them is carried out by an Inertial Navigation System (INS). The INS is comprised of the IMU, i.e. a set of three-axis gyroscopes and three-axis accelerometers and other sensors, e.g. usually a three-axis magnetometer and a pressure sensor; the processor; and software configured to take initial conditions and calibration data and the output from the IMU and other sensors to compute the Navigation.

It is also possible to use other sensors in addition to the IMU, magnetometer, and pressure sensor in order to improve accuracy. For example, in a mobile phone there is a front camera that points towards the user and a rear camera that points towards objects in the room. For the embodiment in which a smartphone, which fits into a socket in the housing that contains the other components of the scanner, at the beginning of the scan the rear camera points towards a particular object in the room. During the scan the rear camera moves with the housing and the movement relative to the object in the image can be tracked using an optical flow method, thereby providing another piece of information to the navigation algorithm that can be used to correct errors.

In embodiments of the invention, the system can be configured to generate accurate scans of ultrasound signals on the skin and to ensure good value images for diagnostic purposes by using a combination of a pressure sensor and IMU and selecting only images that meet optimal values of the speed of scanning and pressure of the scanner against the skin.

These sensors of the inertial measurement unit (IMU) or inertial navigation system (INS) can be implemented using a single chip ASIC that contains all or some of them or as discrete chip that implements each sensor separately or as combinations of sensors.

The IMU provides several types of data:

1. Angles of orientation, which are used to:

a) Provide the user with instructions how to hold the scanner in order to get the best images, b) Provide a physician or other professional with the continuous orientation of the probe at the time a scan was taken in order to facilitate interpretation of the image. This information can be presented as an overlay on the ultrasound image.

2. Speed of the scanner, which is used to:

a) Provide the user with instructions how to move the scanner in order to get the best images. This information can be provided to a remotely located physician so they may be aware of how the scan is performed with all the alerts that the operator experienced.

b) Filter out images that are unlikely to contain useful information. For example, criteria for deleting images could be speed greater than 10 cm/sec, or could also be 1 cm/second in a situation where slow scanning is required in order to detect a specific phenomenon—for example, self-scanning of the inferior vena cava (IVC) in the case of congestive heart failure (CHF) patients.

3. Location of the ultrasound probe head relative to the body's anatomy, which is used to:

a) provide the user with instructions how to scan the whole area of interest in order to fully cover the organ of interest;

b) provide a physician or other professional with the scanner's continuous orientation at the time a scan was taken in order to facilitate interpretation of the image.

The IMU, like other devices, is not perfect. IMU errors, upon integration, form drift, an error that increases over time, and therefore, the error of the computed location and orientation quickly propagates over time. An example can best illustrate the problem. Assume that due to measurement noise and other imperfections, the orientation of the device is known with an error of one milli-radian. This error is considered very small given the quality of, for example, a typical smartphone's IMU. Given this error, the processor misinterprets the accelerometer readings, and interprets the projection of the gravitation as a horizontal acceleration of approximately one $cm/sec^2$. This small acceleration error results in a location error of 18 meters over one minute, clearly well beyond the acceptable error. Thus, the processor must have some additional information, and must assume some restrictions in order to provide meaningful navigation.

The IMU installed in smartphones is based on Micro Electro-Mechanical Systems (MEMS) technology. MEMS technology provides tiny, efficient, affordable sensors, but suffers from inherent imperfections resulting in measurement errors. The errors can be divided into biases and noise. Formally, the only difference is that a bias varies slowly whereas noise varies quickly. However, over the time period relevant to ultrasound scans, and for illustrating the problem, biases can be regarded as constant, and noise can be regarded as absolutely random.

Thus, due to biases, the IMU of a motionless device still produces measurements as if the device is rotating and accelerating. In order to calibrate the IMU and find the biases a calibration procedure must be presented. Still, due to noise, no calibration is perfect, and some residual bias always remains. Also, noise, albeit random, only sums up to zero after an infinite number of measurements. In practice the expected value of the noise is the square root of the number of measurements times the standard deviation of the noise.

As said, the IMUs installed in smartphones are all MEMS based, subject to strict limits of cost, size and energy consumption, and therefore, are very similar to each other. Their noise and bias figures are in principle the same.

As a result of biases and noise, and given the quality of MEMS IMUS, the navigation process must integrate more measurements, and utilize some prior assumptions, in order to mitigate the IMU errors. When scanning with the scanner, the distances moved are small and the scanning speed is relatively slow, which frequently results in the noise generated in the IMU being larger than the signal. Typical distances for these scans are in the range of several millimeters and up to several tens of centimeters and typical speeds of 1 mm/sec to several centimeters per second. Thus, successful navigation relies on optimal calibration allowed by the system, the mission, and the user, and on the integration of other available cues.

Some bias errors are calibrated for at the manufacturing level. However, some biases vary over time and must be calibrated prior to use. In the case of the scanner described herein, the calibration process is limited to simple steps that the user can easily perform. A prior assumption that can be made is that the user cooperates by holding the scanner such that she/he faces the display on a horizontal table.

If the scanner is placed on a horizontal surface, the acceleration axis should be equal to 9.81 downward, so if a different value than 9.81 is measured, the processor can calibrate the offset and add the offset to each measurement. If the user is required to calibrate the IMU, then, after the system is activated before the beginning of a scanning session, the user is prompted, either by the software in the processor or by a remotely located technician, how to calibrate the gyroscopes and accelerometers. IMU's, especially those made by MEMS technology, must be calibrated before every use as the calibration values vary from day to day and each time they are turned on.

A calibration procedure comprising seven phases will now be described. This procedure is one of many that can be used with the scanner and is only meant to illustrate the principles involved. The inventors have used other calibration procedures comprising fewer than seven phases and anticipate that other procedures involving, for example a different order of the phases or more or less than seven phases, can be devised and used, and the selection of the actual calibration method is not essential as long as it yields the required calibration result. In many situations, especially when only slow motion is allowed and the user keeps the screen toward her within several degrees, a one-step calibration, in which only the offset of the gyroscopes is estimated, provides excellent results. In this protocol, the IMU is held still for some time, and the output of the sensors is recorded. The average output of the gyroscopes is taken to be their offset, and the variance of each sensor is taken to be its noise. The Earth rotation, approximately 15 degrees per hour, is usually negligible compared to the gyroscopes offset.

For this example, a coordinate system is selected. In this coordinate system the positive Z-axis points up, the positive Y-axis points towards the right, and the positive X-axis points forward. The letter T is used for the duration of the calibration, it can be, for example, 1, 3, 5, or 10 seconds or longer pending on the type of the IMU. The value of T is a compromise between the degree of accuracy and the patience of the user. The procedure has the following seven phases:

Phase 1: Hold the scanner still for T seconds.
Phase 2: Rotate the scanner around the Y axis such that the rotation is completed and the scanner is stationary in the new orientation, within T seconds
Phase 3: Hold the scanner still for T seconds, then rotate back.
Phase 4: Rotate the scanner over around X axis within T seconds.
Phase 5: Hold the scanner still for T seconds, then rotate back.
Phase 6: Rotate the scanner over around Z axis within T seconds.
Phase 7: Hold the scanner still for T seconds, then rotate back.

The data from the three accelerometers and three gyroscopes are collected by the electronics and transferred to the processor during these seven phases. An example of gyroscopes data is shown in FIG. 1.

Figure 1:
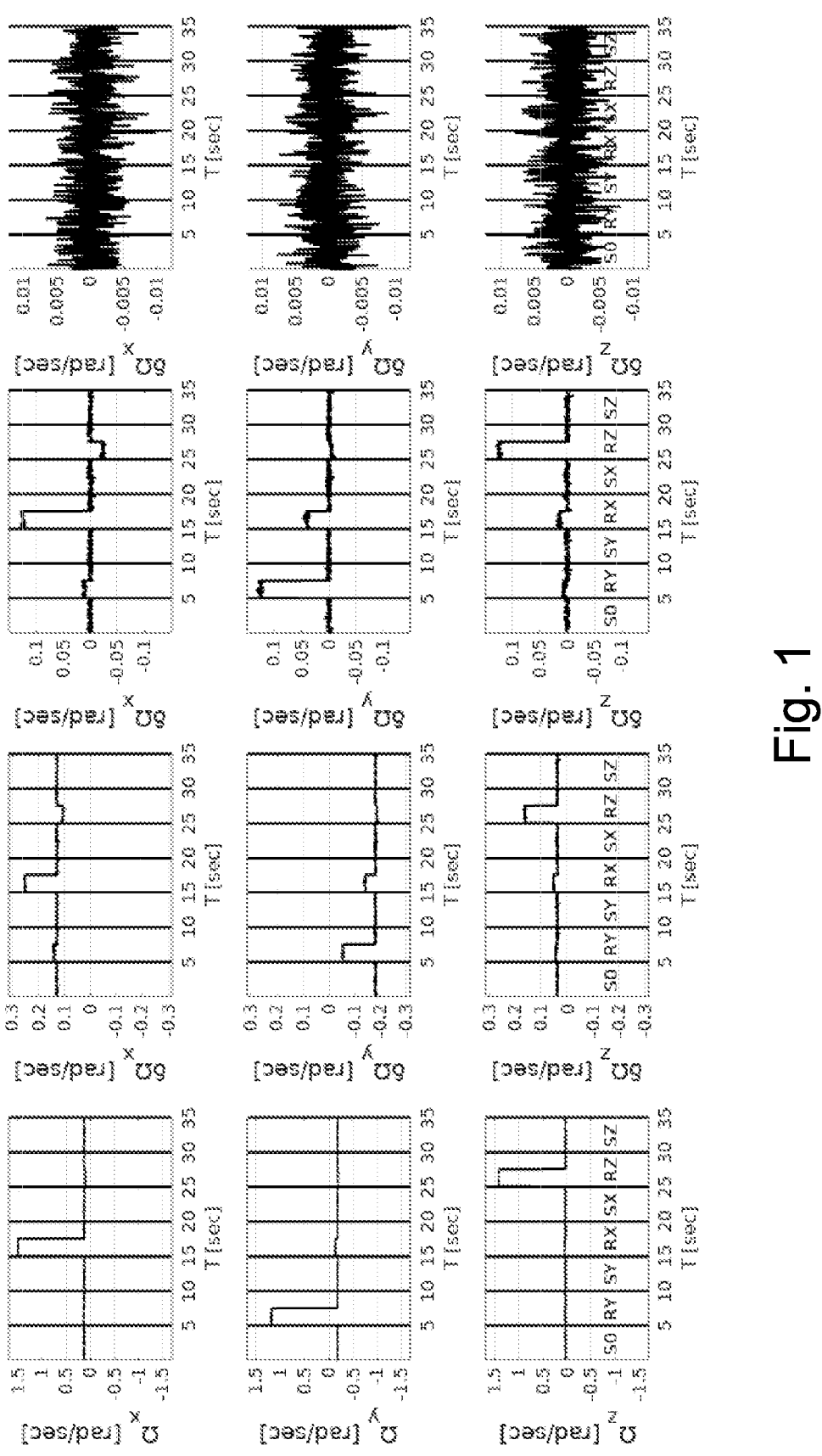
FIG. 1 shows four columns each containing plots of data relating to the calibration process.

FIG. 1 shows four columns each containing plots of data relating to the calibration process. In each column, the three rows refer to the three gyroscopes: x, y and z. In each plot of FIG. 1, the horizontal axis is the time of measurement and the vertical axis is the measurement taken from the gyroscopes or the error of this measurement. Vertical lines mark borders between the seven phases, wherein phases are labeled as follows: the $1^{st}$ S0, the $2^{nd}$ RY, the $3^{rd}$ SY, the $4^{th}$ RX, the $5^{th}$ SX, the $6^{th}$ RZ, and the $7^{th}$ SZ. The first letter, either S or R, refers to either "stationary" or "rotating" situation. The second letter, either X, Y or Z, refers to the axis around which the rotation is taken or the axis around which a rotation was taken prior to the stationary situation.

Referring to FIG. 1, one can see how the data is interpreted. The leftmost column contains the data collected from the gyroscopes. At the first phase, S0, at time 0-5 seconds, the device is stationary and the gyroscopes output their offset and any constant rotation, e.g., the Earth rotation. At the second phase, RY, at time 5 to 10 seconds, the first 2.5 seconds shows a 180 degrees rotation around the y-axis. Thus, y-gyro shows a large signal. And so on for the other phases.

The next column, the second from the left, shows the error of the measurements. Note that in this case the error is known since every gyroscope senses either zero rotation, or a known angular velocity of 180 degrees over 2.5 seconds period, or approximately 1.26 rad/sec. In this column one can see three features of the signal. The offset is better seen, there is signal at time of rotation on axes other than the axis of rotation, and the output of the rotating gyro is different than expected. The latter two phenomena result from cross-axis measurement and scale factor errors.

The first phase, S0, in this example between 0 and 10 seconds, is stationary, and therefore, apart from a small contribution of the rotation of the Earth, should produce zero. However, it can be seen that, in this example, the measurements are offset at approximately [0.12, −0.18, 0.02] rad/sec including less than 10 rad/sec for the rotation of the Earth. At the third phase, SY, data are taken from the same sensors after the sensor was rotated 180 degrees around y-axis, and in this case the contribution of the rotation of the Earth for axis x and z are inversed. Thus, averaging the data at S0 and SY gives an estimate for the offset of the x- and y-gyro. Similar protocol applies to the other axes using other rotations.

The next column, the third from the left, shows the same data as in the previous two columns after the computed offset is removed. Accordingly, stationary states now show 0 rad/sec plus some noise.

Inspecting the third column one can compute the cross-axis effect. For example, the output of the x-gyro during RY phase should have been zero, and is actually approximately 0.013 rad/sec. The ratio between the average output of the x-gyro, approximately 0.013 rad/sec, and the average output of the y-gyro, approximately 0.126 rad/sec produces the cross-axis effect between y and x axes, which is approximately 0.01. Similarly, one can work out the relations for all nine cross-axis possibilities.

The scale factor can also be computed from the data in this column by comparing the error to the expected result. For example, an error of 0.125 rad/sec is seen at the second row at phase RY. This error is approximately 0.1 of the signal, and therefore, the scale factor is 1.1.

The scale factor and the cross-axis can be combined into a matrix. Multiplying the original results by the inverse of this matrix and subtracting the original data produces the results on the last column, which only contains noise. This noise is conveniently used to estimate the detector noise required by the Extended Kalman Filter.

Note that time-constant angular velocity, as shown here, is only for the clarity of the example. Replacing every computation by its average over the duration of the phase produces the same results.

The algorithm used by the software in the processor for calibrating the gyroscopes' offsets is:
1. O_s0=mean of the data collected at phase 1 for each of three gyroscopes.
2. O_sy=mean of the data collected at phase 3 for each of three gyroscopes.
3. O_sz=mean of the data collected at phase 7 for each of three gyroscopes.

4. Compute:

a) Offset for $$x\text{-axis} = B_x^\omega = (O\_s0_x + O\_sy_x)/2$$

b) Offset for $$y\text{-axis} = B_y^\omega = \left(O\_s0_y + O\_sy_y\right)/2$$

c) Offset for $$z\text{-axis} = B_z^\omega = (O\_s0_z + O\_sy_z)/2$$

Wherein, the subscripts x, y, z refer respectively to the data from the x, y, and z gyroscopes.

The algorithm used by the software in the processor for calibrating the gyroscopes' scale factors is:

5. O_ry=mean of the data collected at phase 2 for each of three gyroscopes.

6. O_rx=mean of the data collected at phase 4 for each of three gyroscopes.

7. O_rz=mean of the data collected at phase 6 for each of three gyroscopes.

8. Compute:

a) Scale factor for $$x\text{-axis} = (O\_rx_x + B_x^\omega) * T / pi$$

b) Scale factor for $$x\text{-axis} = \left(O\_rx_y + B_y^\omega\right) * T / pi$$

c) Scale factor for $$x\text{-axis} = (O\_rx_z + B_z^\omega) * T / pi$$

The algorithm used by the software in the processor for calibrating the gyroscopes' cross-axis sensitivity is based on the matrix $C^\omega$ 9. where:

a)

$$C_{x,x}^\omega = (O\_rx_x + B_x^\omega) * T / pi$$

b)

$$C_{x,y}^\omega = \left(O\_rx_y + B_x^\omega\right) * T / pi$$

c)

$$C_{x,z}^\omega = (O\_rx_z + B_x^\omega) * T / pi$$

d)

$$C_{y,x}^\omega = \left(O\_rx_x + B_y^\omega\right) * T / pi$$

e)

$$C_{y,y}^\omega = \left\{O\_rx_y - B_y^\omega\right\} * T / pi$$

f)

$$C_{y,z}^\omega = \left\{O\_rx_z - B_y^\omega\right\} * T / pi$$

g)

$$C_{z,x}^\omega = \left\{O\_rx_x - B_Z^\omega\right\} * T / pi$$

h)

$$C_{z,y}^\omega = \left\{O\_rx_y - B_Z^\omega\right\} * T / pi$$

i)

$$C_{z,z}^\omega = \left\{O\_rx_z - B_Z^\omega\right\} * T / pi$$

The algorithm used by the software in the processor for computing the three projections of the gravity on the three accelerometers in initial body coordinates is:

1. A_s0=mean of the data collected at phase 1 for each of three accelerometers.

2. A_sy=mean of the data collected at phase 3 for each of three accelerometers.

3. A_sz=mean of the data collected at phase 5 for each of three accelerometers.

4. Compute:

a) x-projection of gravity=A_ref$_x$=(A_s0$_x$−A_sy$_x$)/2 b) y-projection of gravity=A_ref$_y$=(A_s0$_y$−A_sz$_y$)/2 c) z-projection of gravity=A_ref$_z$=(A_s0$_z$−A_sy$_z$)/2

An Extended Kalman Filter (EKF) is now used to estimate the orientation of the scanner.

The state vector at time k ($\hat{x}_k$) has seven members: three components of the angular velocity in body-frame coordinates $$(\hat{\omega}_k^b)$$

and four components of the quaternion ($\hat{q}_k$) representing the orientation of the scanner or the rotation of the scanner's body-coordinates relative to the room's assumed inertial coordinates.

$$\hat{x}_k = \begin{bmatrix} \hat{\omega}_k^b \\ \hat{q}_k \end{bmatrix}$$

The transition function, predicting the next step state vector is:

$$\hat{x}_{k+1,predicted} = \begin{bmatrix} \hat{\omega}_k^b \\ \frac{1}{2}\hat{q}_k \otimes \omega_k^b dt \end{bmatrix}$$

where dt is the time step and $\otimes$ is the quaternion multiplication operator.

The measurement vector is:

$$Z = \begin{bmatrix} a_k^b \\ \hat{\omega}_k^b \end{bmatrix}$$

where $$a_k^b$$

is the output of the accelerometer triad at time k, which in turn equals to:

$$a_k^b = C^a\left(\hat{g}^b + \delta a_k^b\right) + B^a + u^a$$

here $C^a$ is a 3×3 matrix whose diagonal consists of the scale factors of the accelerometers triad, the off-diagonals components are the cross-axis sensitivity of the accelerometers, $B^a$ is the biases of the accelerometers, $$\delta a_k^b$$

is the specific force per unit mass applied due to real accelerations, $\hat{g}^i$ is gravity in body coordinates, and $u^a$ is noise. As an approximation $\hat{g}^i$ is taken from A_ref computed at the calibration process.

Similarly, $$\hat{\omega}_k^b = C^\omega(\hat{\omega}^i) + B^\omega + u^\omega$$

The predicted measurement is:

$$\hat{Y}_{k+1} = \begin{bmatrix} \hat{g}^b \\ \hat{\omega}_k^b \end{bmatrix} = \begin{bmatrix} \hat{q}_k \otimes \hat{g}^i \otimes \hat{q}_k \\ \hat{\omega}_k^b \end{bmatrix}$$

$C^a$ and $B^a$, as well as $C^\omega$ and $B\omega$ are those calculated at the calibration process.

Implicitly, this filter assumes that the specific force $$\delta a_k^b$$

(acceleration without gravity) is very small compared to the gravitation, and therefore the accelerometer output vector points down. This situation caps a strong limit on the rotation error thus restraining gyroscope drift.

Figure 2:
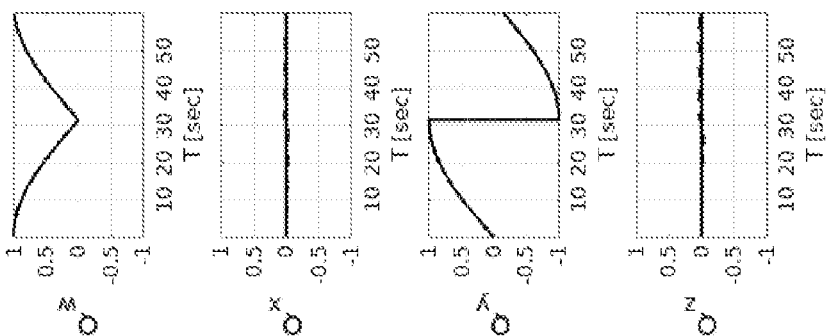
FIG. 2 shows the results of estimating the orientation of the scanner by applying an Extended Kalman Filter to the calibrated gyroscope and the accelerometer data.
Figure 2:
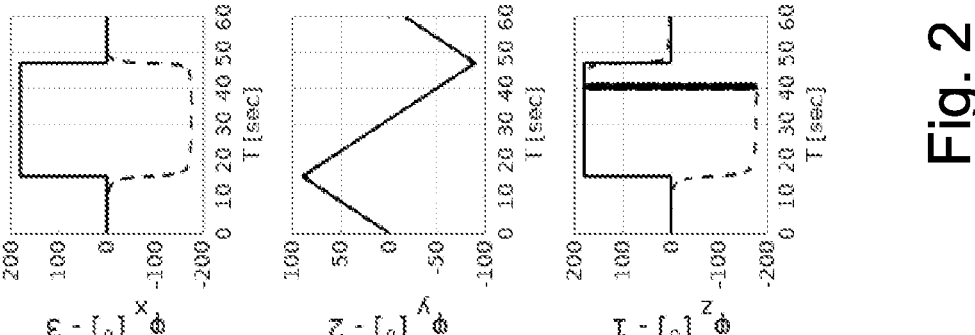
Figure 2:
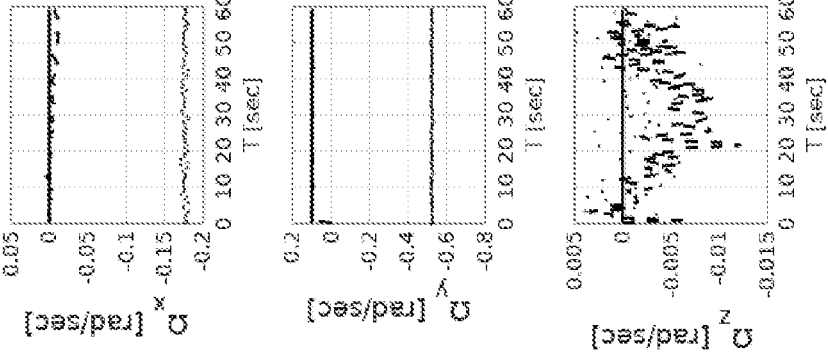

FIG. 2 shows the results of estimating the orientation of the scanner by applying an Extended Kalman Filter to the calibrated gyroscope and the accelerometer data. The left most column shows the output of the gyroscope with a dotted line, the Extended Kalman Filter (EKF) estimation of the rotation with a broken line, and the true rotation with a solid line. Each row depicts one axis: x, y and z. The left column relates to the angular velocity as measured at body-fixed coordinates. Looking for example at the x-gyro at the top, the true rotation is zero. The sensor produces approximately −0.18 rad/sec, which results from offset. The true rotation and the calibrated signal are close together near zero. Note that for y-axis a true rotation of 0.1 rad/sec is applied. All measurements enclose some noise of the order of magnitude of several milliradians per second. The noise is more easily seen at the output of the z-gyro because without large offset or rotation the scale of the figure reduces to noise level. The rightmost column shows the four elements of the quaternion used in the EKF to estimate the orientation.

Again, solid lines and broken lines are used for the real and the estimated quaternion, and they fall very close to each other. The middle column depicts the orientation in Euler angles, which are easier to interpret. Since an angular velocity of 0.1 rad/sec is applied the y-angle advances at this velocity. The solid and broken lines are so close that they cannot be distinguished. The dynamics of the error can better be seen on the x- and z-angles where some error accumulates when y-angle nears 90 degrees. Of course, 180 degrees and minus 180 degrees refer to same angle and are not an error. The accumulation of error when y-rotation nears 90 degrees is not accidental, and results from numerical effect. The translation of quaternion to Euler angles uses inverse trigonometric functions and is very sensitive near 90 degrees.

Figure 3:
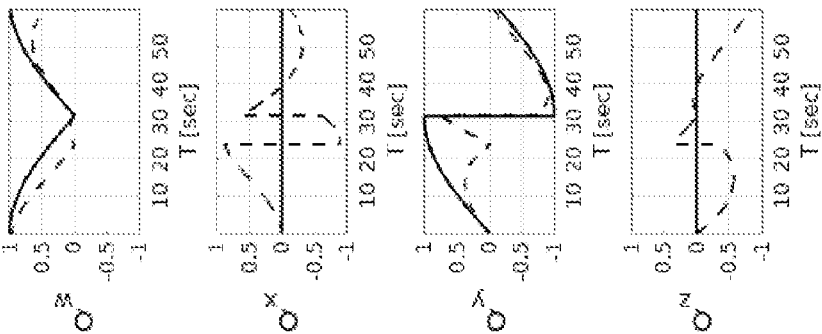
FIG. 3 repeats a test similar to the one shown in FIG. 2, but the measurements are fed into the EKF without calibration.
Figure 3:
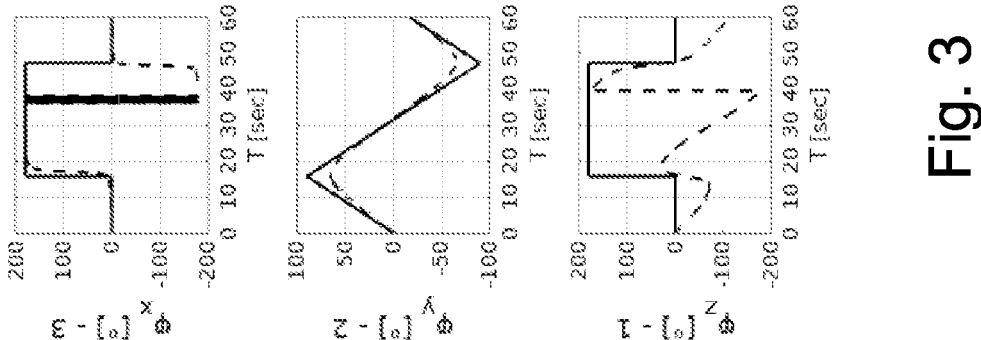
Figure 3:
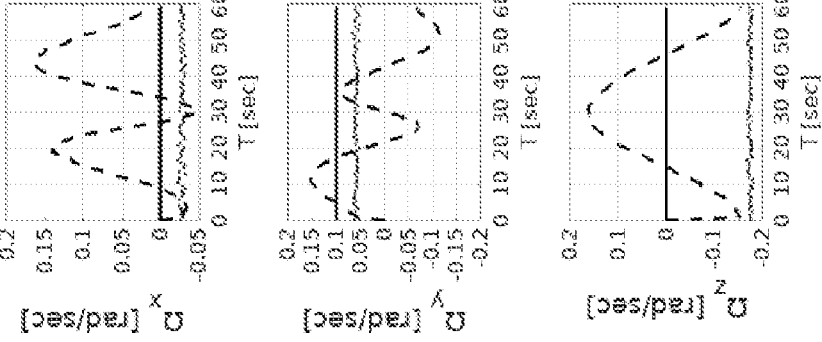

FIG. 3 repeats similar test to the one shown in FIG. 2, but the measurements are fed into the EKF without calibration. One can observe the errors in the signal, the offset at the y-axis and the cross-axis effect on the others. These errors translate into a large error in the y-angle, and observable errors in the x- and z-angles.

The ultrasound scan depends on holding the scanner such that some pressure is exerted on the skin. When the pressure drops, the scanner produces a flat image. The processor analyzes the image, and upon concluding that the picture is flat or using similar criteria such as measuring the variance of the brightness of the image over some region of interest, instead of the entire picture. If the brightness is smaller than a threshold value, it issues an instruction to the operator to increase pressure. In an embodiment this instruction may include, as an example, the appearance of a down-pointing arrow on the display screen with vocal instruction to increase pressure on the skin.

Figures 7A, 7B, 7C:
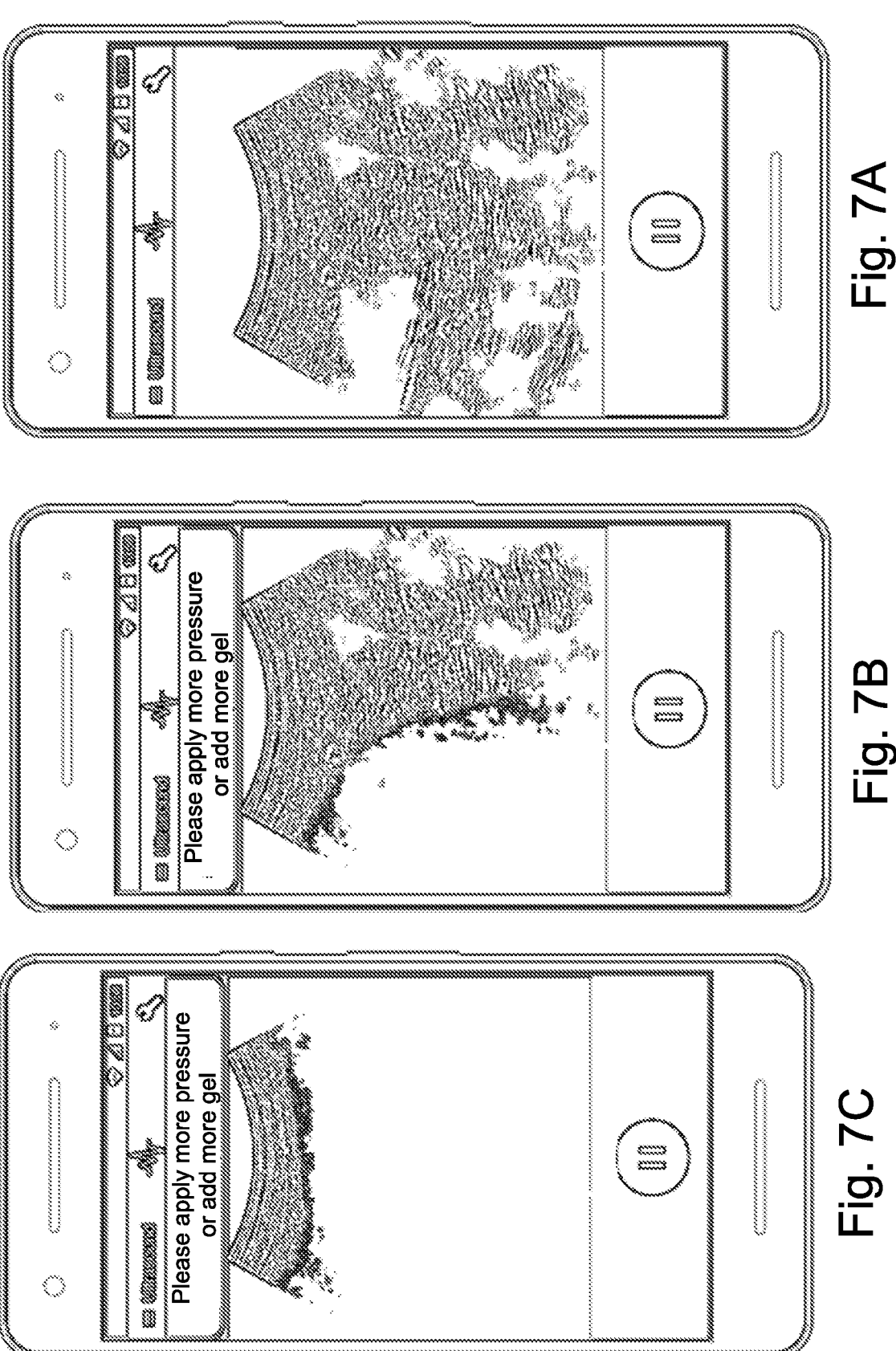
FIGS. 7A-7C are screenshots showing the effect on the images of insufficient coupling between the ultrasound probe head and the patient's body.

It is common to use a water-based gel in order to provide a smooth media for the ultrasound beams to propagate from the probe to the body, otherwise the beams will attenuated when passing through air. Using the resulting signal or image it is possible to determine whether the coupling between the probe and the body is sufficient. This, for example, can be determined by the weakening of the signals returning to the probe or by the weakening of the resulting ultrasound image. FIG. 7A is a screenshot showing good coupling between the ultrasound probe head and the patient's body and FIG. 7B and FIG. 7C show examples of insufficient or partial coupling. This process can be carried out in the mobile device processor or in the controller of the AFE, in a component of the device containing the ultrasound transducer, or in external software.

The speed of the scan can be calculated from the angular velocity. The processor assumes motion perpendicular to the surface of the body. For prenatal exams, the body can be modeled as a sphere, for example $R_0$=20, 30, 40 or even 70 cm for obese patients. The radius can be better approximated based on the patient's BMI and stage of the pregnancy. The speed can be approximated as:

$$\hat{V}_k = \hat{\omega}_k^b \times R_k^b$$

where $$\hat{\omega}_k^b$$

is the angular velocity at body coordinates, estimated by the filter, and $$R_k^b$$

is computed as $R_0 \hat{u}_x$ and $\hat{u}x$, is the unit vector pointing down from the scanner. Under normal conditions the angular velocity is dominantly along the scanner y-axis, i.e., the scanner moves right to left or left to right along a sphere, and the speed is approximately $$R_0 \hat{\omega}_{y_k}^b.$$

Figure 4:
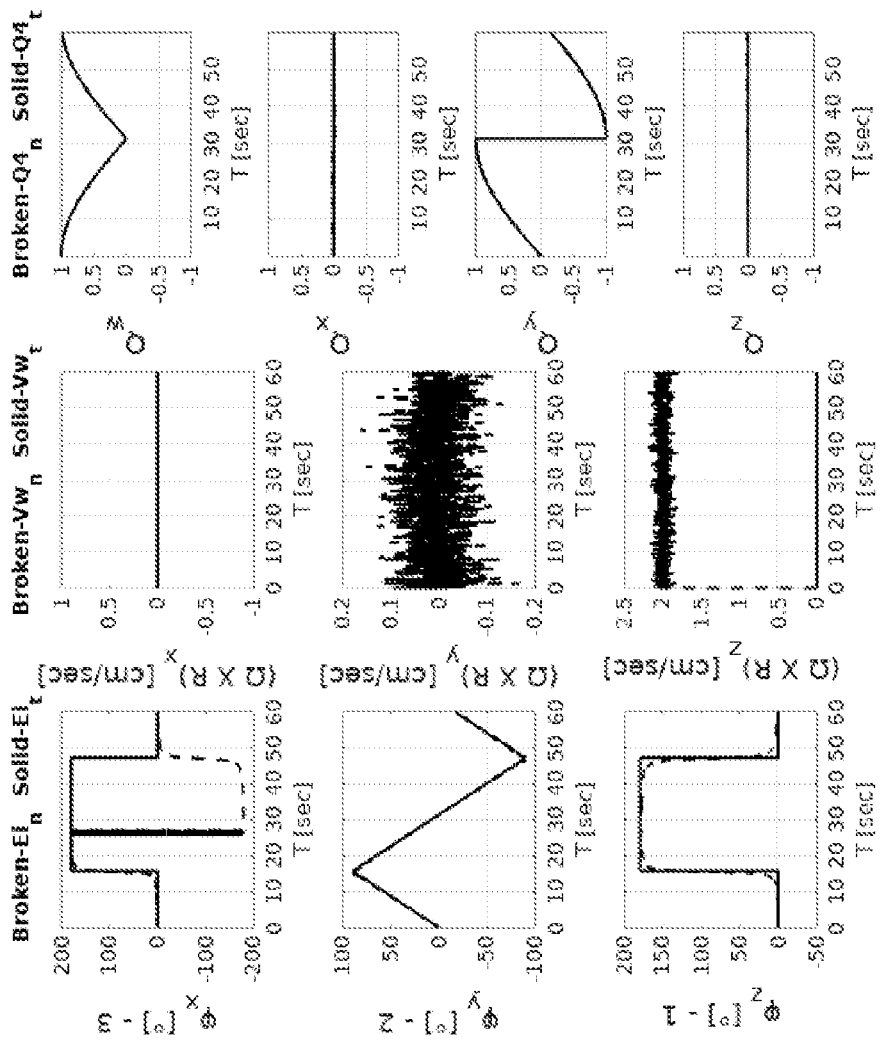
FIG. 4 shows the angular velocity with which the scan is being carried out, and the tangential velocity that is derived from the angular velocity.
Figure 4:
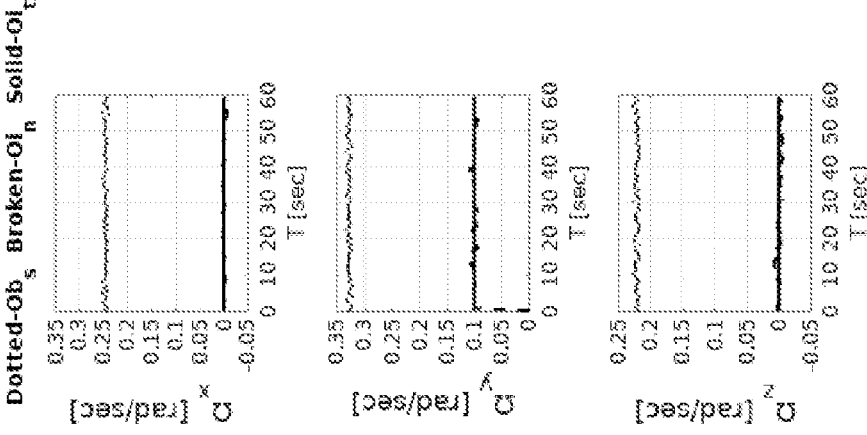

FIG. 4 shows the angular velocity with which the scan is being carried out, and the spatial velocity that is derived from the angular velocity. The third column of the figure shows the three components of the velocity in radial coordinates along the belly of a pregnant patient. The X-axis refers to radial motion from the center of the belly to the outside. This motion is by assumption zero. The y-axis refers to motion across the belly from bottom to top, and z-axis refer to motion from right to left. The other columns show the same information as the tree columns in FIG. 2 and are shown for reference. The range of permitted velocities is a characteristic of the scanner, and is typically several centimeters per second. This slow motion produces radial acceleration of as little as one millimeter per second squared, which means that the acceleration of gravity can be used by the EKF as a good approximation of the acceleration in the downward direction. Thus, when the computed velocity is not within a permitted range, the scan is discarded and an instruction is issued to the patient to go slower.

Combining the speed and orientation, the scanner can ensure that the user is instructed to cover a predetermined range of angles, and to do it within the permitted velocity range. Adding the quality of the image produced by the image processing a proper pressure on the skin is also maintained. Altogether this ensures a good examination.

Figure 8:
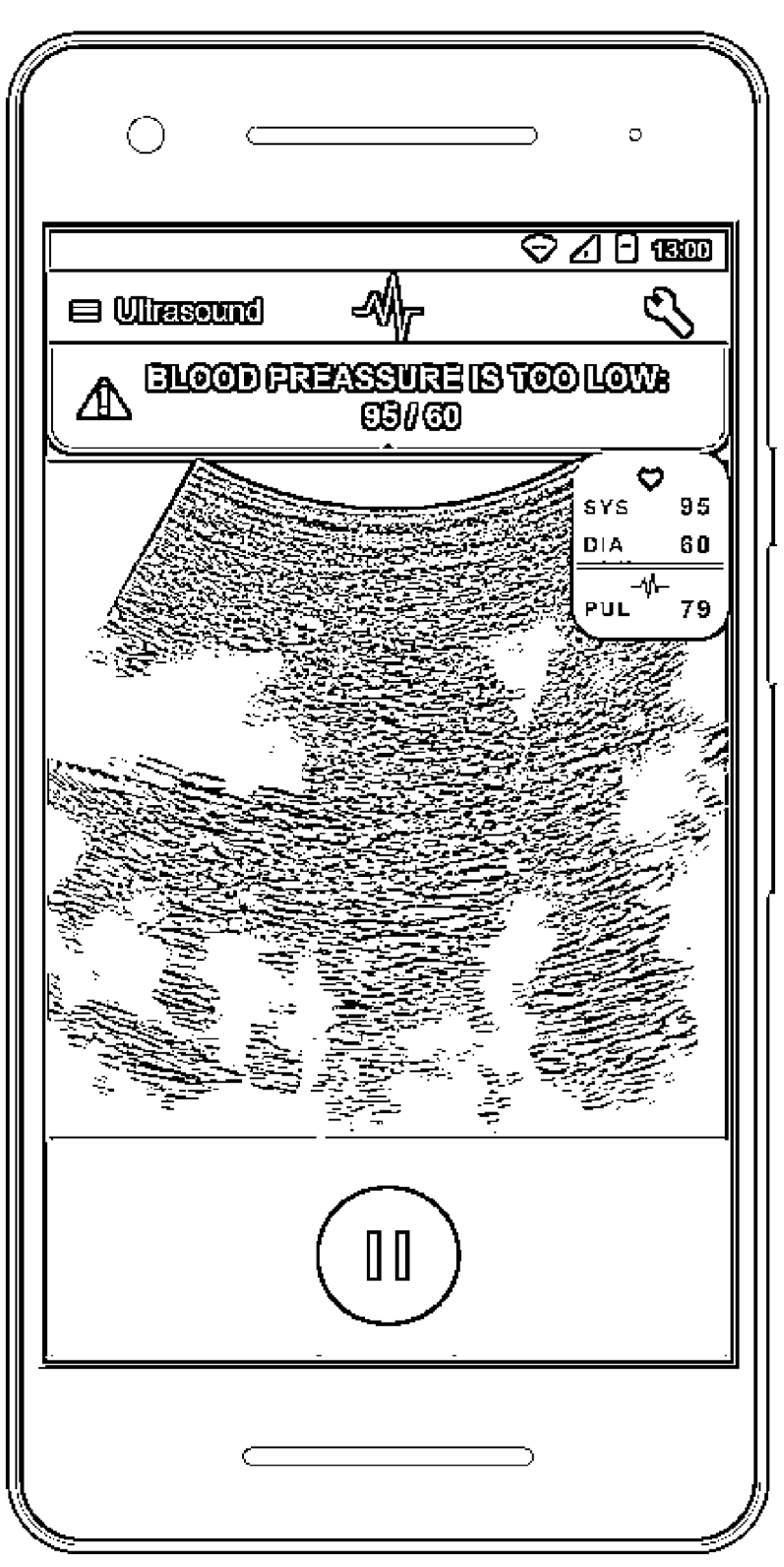
FIG. 8 is a screen shot showing the results of a blood pressure measurement overlaid on the scan.

Since in many cases a physician or other trained healthcare professional will either directly observe the results of the scan or be provided with the scans for analysis, it is important that they be provided with all of the information necessary to understand the data they are provided. In the case of prenatal scans, blood pressure is measured at every prenatal visit. So at home, the blood pressure of the patient should also be measured and the result of the measurement added to the record of the ultrasound scans. High blood pressure in pregnancy is an important diagnosis and indicator for preeclampsia and is very important in determining how the rest of the pregnancy is managed prior to delivery, the timing of delivery, risk of complications, and long-term maternal outcomes. It also affect the way that a sonographer will relate to the scans since, if the fetal heartbeats are low and the mother's blood pressure is low it is possible that the fetus is healthy; however if the fetal heartbeats are low and the mother's blood pressure is normal, this indicates that the fetus is probably sick. FIG. 8 is a screen shot showing an embodiment of how the results of a blood pressure measurement can be displayed to a physician or other trained healthcare professional both as a written message and as an overlay on the scan.

The scanner is a "black box" as far as the operators of the scanner are concerned. The algorithms discussed above are all useful only to the internal working of the system, whose processor is programmed to utilize them in order to generate instructions to the patient to guide them through the process of collecting ultrasound scans that are of sufficient quality to provide useful information. The patients only have to follow the visual or audible instructions that they receive from the components of the system or from a sonographer in the case of Telemedicine. It is also possible to show video instructions by means of animations.

In general, a typical set of instructions issued by the system to guide an operator to perform a scan will comprise the following:

a) instruct the patient to carry out a calibration procedure, if necessary, by guiding the patient through the procedure e.g. the single step or the seven stages of the calibration procedures described herein;

b) instruct the patient to measure her blood pressure, using a blood pressure meter;

c) instruct the patient to take additional tests;

d) instruct the patient how to position themselves to take the scan, e.g. horizontally on their back for a pre-natal scan;

e) instruct the patient to position the scanner at a location that will serve as the center of a patient coordinate system, e.g. on the navel for a prenatal exam, between the nipples for a heart scan, of three finger widths from the nipple on the right or left sides for a scan of the lungs;

f) instruct the patient to position the scanner with the screen facing them;

g) provide the patient with instructions including the direction in which to move the scanner over the surface of their body, how far to move in each direction, the speed with which the scanner should be moved, and the amount of force they should exert to press the scanner against the body;

h) advise the patient that the session is over when enough images of sufficient quality have been collected; and i) if not done so automatically, advise the patient to forward the images to a health care professional to be interpreted.

In some embodiments of the invention, the output of the scanner may be sent directly to a healthcare professional, e.g. the patient's personal physician, in real time or after they are acquired, and some or all of the instructions to the patient may be sent by the physician, especially if a particular region of the anatomy has to be studied in greater depth than is normally possible from general scans. As an aid to the physician, in some embodiments of the system, software in the processor is configured to overlay an image of the scanner on top of the ultrasound scans. In other embodiments, the processor is configured to relay the instructions that are sent to the operator during the scan so the physician can understand what instruction was presented and at what time with respect to the images.

Example 1: Coupling Alert

The following exemplifies a coupling alerting procedure according to one particular embodiment of the invention. The procedure involves the following steps:

a. Image acquisition—Construction of the ultrasound image from the echoes received from the body organs to the transducer.

b. Image pre-processing—At the beginning of the process, the frames undergo image pre-processing that normalizes the variance between frames from different scans.

c. Total Black Frame (TBF) test—following the image pre-processing the algorithm performs a TBF test. In the TBF test, the percentage of pixels that are absolute black in the entire current frame are examined, in order to find frames that qualify for a TBF condition.

d. Coupling condition classification—The coupling condition of any side (left/right) of each frame is made by a decision tree classifier.

e. Buffer test—Each classification is saved in a buffer on length of 16 decisions. If 80% of the decisions indicate an insufficient coupling, the user is instructed to improve skin contact or add more gel.

f. Displays an alert to the operator—While performing a scan, the user receives real-time feedback regarding the coupling condition. In case of 80% frames with insufficient coupling, the user is instructed to improve skin contact or add more gel.

g. Add image to recording—If good coupling is detected, the frame is recorded.

h. Displays an alert to the operator (TBF)—If no coupling is identified, the system guides the user to hold the cradle tighter to the skin.

i. Drop image from recording—in TBF cases the frame is not be, thus improving the received image.

j. Display image on screen—all images are displayed on the screen (TBF, insufficient coupling and good coupling).

Figure 10:
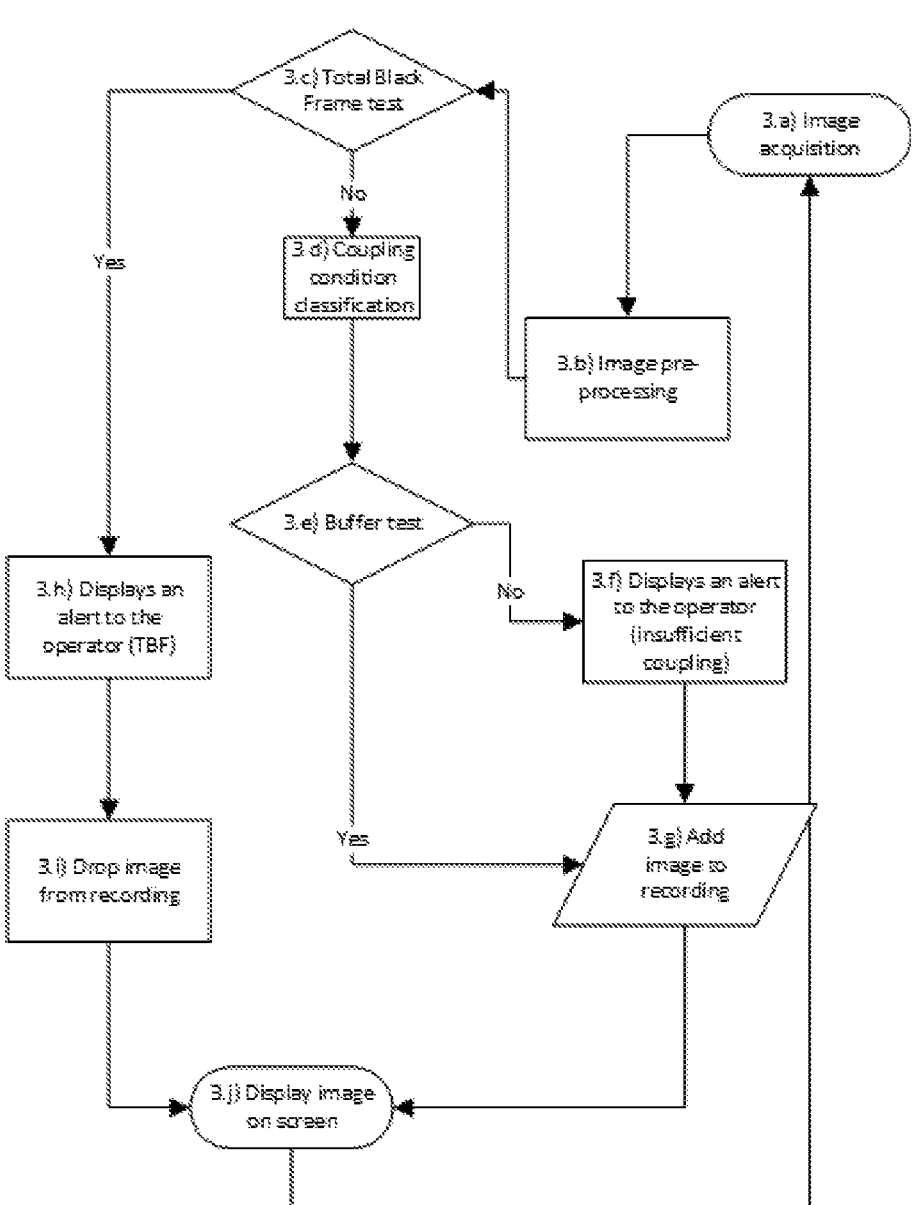
FIG. 10 is a flow chart of a coupling alert process.

The process is shown, in flow chart form, in FIG. 10.

Example 2: "Scan Too Fast" Alert

The following illustrated a procedure for dealing with a user who is moving the housing too fast to produce a good quality scan.

From the scanned image the following two steps are performed to acquire a value for the scan speed:

a. Detecting a change in a large portion of the image; and b. Detecting the optical flow to obtain the speed.

The first step is aimed at distinguishing between the embryo's movements, and the scanner's movement. The embryo's movements are localized and so they do not change a large portion of the image. In contrast, a scanner movement will change all the image at once. To estimate the change, a temporal standard deviation is calculated over 6 frames. If significant change is detected in more than 0.5% of the total scan pixels, this signifies that a movement has been made.

To evaluate an overall change in the picture, a change per second in pixel intensity is evaluated across the image. A pixel temporal standard deviation is used as an estimator for change. For an image I(x, y, n) where "n" is the number of frames, and each frame is taken in time t(n). The following calculation is used to evaluate change:

$$\sigma(x, y, n) = \frac{1}{6}\sqrt{\sum_{i=n-5}^{n} I(x, y, i)^2 - \left(\sum_{i=n-5}^{n} I(x, y, i)\right)^2}$$

This yields a measurement of the amount of change per frame. To evaluate the change in time the value is normalized by the mean FPS $$\sigma^*(x, y, n) = \sigma(x, y, n) \cdot \frac{6}{\sum_{i=n-5}^{n} t(n) - t(n-1)}$$

In the next step the number of pixels that have change dramatically is calculated:

$$C(x, y, n) = \begin{cases} 1; & \sigma^* > Th \\ 0; & \text{else} \end{cases}$$

where Th is a threshold empirically selected to distinguish between noise- and motion-related changes. In order to determine the required threshold value, in one embodiment the mean standard deviation between 10 sequential frames is calculated for 100 scans, which have been taken with the ultrasound device of the invention. It should be taken when the device is held still, for instance on a pregnant women abdomen with no significant fetal movements. Th value are calculated as the mean and three standard deviations of the calculated values.

Now the sum of C is calculated to understand which percent of the image has changed.

If $$\frac{\sum_{x=1}^{X}\sum_{y=1}^{Y} c(x, y, n)}{XY} > 0.5,$$

the frame is considered as a moving frame.

For a moving frame, an optical flow $v_x$, $v_y$ is calculated using the Lucas-Kanade method with pyramids. Corners in the centre of the image are used for calculation using Harris corner detector.

The optical flow gives the speed per frame. In order to attain the speed in time it should be normalized by the FPS.

$$[V_x^+, V_y^+] = \frac{[V_x, V_y]}{t[n] - t[n-1]}$$

Although embodiments of the invention have been described by way of illustration, it will be understood that the invention may be carried out with many variations, modifications, and adaptations, without exceeding the scope of the claims.

The invention claimed is:

1. A method for acquiring ultrasound images of internal organs of a human body, comprising:

providing a system comprised of a scanner and at least one inertial measurement unit (IMU) located within the scanner, the scanner being movable by an operator over a surface of a patient's body to obtain the ultrasound images, and providing, by the system, instructions for an untrained user to operate said scanner to allow scans to be performed, wherein the instructions issued by the system guide an operator to perform a scan and include:

(i) providing audible or visual instructions to the operator to position the scanner at a location that will serve as the center of a patient coordinate system;

(ii) providing the operator with audible or visual instructions including the direction in which to move the scanner over the surface of the patient's body, how far to move the scanner in each direction, the speed with which the scanner should be moved, and the amount of force to be exerted by the scanner against the patient's body; and (iii) indicating to the operator that a predetermined number of images have been collected.

2. The method of claim 1, further comprising transmitting acquired ultrasound images to a remote location for analysis by a healthcare professional.

3. The method of claim 1, further comprising providing circuitry adapted to perform two-way communication between the operator and a remote individual or a non-monitored system, the two-way communication being at least one of audio-visual communication or video communication.

4. The method of claim 3, wherein the non-monitored system comprises automated, image analysis circuitry, and wherein an output of an automated analysis is provided to at least one of the operator or a healthcare professional.

5. The method of claim 1, wherein when the scans are performed by an operator, two-way video communication between the operator and a health care professional is enabled.

6. The method of claim 5, further comprising sending an output of the system directly to at least one of a remote healthcare professional or a non-monitored system professional in real time or after the images are acquired.

7. A system for allowing a non-skilled user to acquire ultrasound images of internal organs of a human body, the system comprising:

a scanner, at least one inertial measurement unit (IMU) associated therewith, a user interface comprising a display screen and means to accept user input, and a processor containing software, wherein the software is configured to:

produce ultrasound image data;

analyze the ultrasound image data;

display on the display screen only those images which, based on said analysis, contain an anatomical structure or depict a physiological condition;

instruct the operator to hold the housing of the scanner in a predetermined manner;

compute the location and attitude of the scanner;

issue instructions about an amount of pressure to be exerted on the skin based on said analyzing of said ultrasound image data; and provide instructions for how to move the scanner correctly in order to obtain images with sufficient resolution that an anatomical structure or a phycological condition is discernible, wherein the processor and software of the system are configured to issue the following instructions to an operator to guide the operator to perform a scan:

(i) audible or visual instructions to position the scanner at a location that will serve as the center of a patient coordinate system;

(ii) audible or visual instructions regarding the direction in which to move the scanner over the surface of the patient's body, how far to move the scanner in each direction, the speed with which the scanner should be moved, and the amount of force to be exerted by the scanner against the patient's body; and (iii) instructions to indicate to the operator that a predetermined number of images have been collected.

8. The system of claim 7, further comprising an electronic communication component, the electronic communication component being one or more of USB, Lightning, fiber optic, Wi-Fi, UWB, Bluetooth, or IR.

9. The system of claim 7, further comprising an IMU independent component adapted to generate an alert indicative of insufficient coupling between the scanner and the patient's body.

10. The system of claim 7, further comprising an IMU independent component adapted to generate an alert regarding a scanning speed.

11. A method of conducting an ultrasound examination, the method comprising:

analyzing, by a processor containing software, ultrasound image data;

issuing, by the processor, digital instructions via a user interface, said instructions including:

an amount of pressure to be exerted via a scanner against a patient's body based at least in part on said analyzing;

a direction in which to move the scanner across a surface of the patient's body;

how far to move the scanner across the surface of the patient's body; and a speed with which the scanner should be moved across the surface of the patient's body; and providing the instructions to an operator for how to operate the scanner.

12. A system for acquiring ultrasound images of internal organs of a human body, the system comprising:

a scanner and at least one inertial measurement unit (IMU) associated therewith;

a user interface; and a processor containing software, wherein the software is configured to:

analyze ultrasound image data generated by the scanner;

issue instructions via the user interface, said instructions indicating an amount of pressure to be exerted on a patient's body via the scanner based on said analyzing and a speed with which to move the scanner across a surface of the patient's body; and provide the instructions to an operator for how to operate the scanner.

13. A system according to claim 12, wherein said instructions indicate adjustment of location and attitude of the scanner on the patient's body.

14. A system according to claim 12, wherein said instructions indicate a direction in which to move the scanner across a surface of the patient's body.

15. A system according to claim 12, wherein said instructions indicate a distance to move the scanner across a surface of the patient's body.

* * * * *